(12) United States Patent
Thapliyal

(10) Patent No.: US 9,801,741 B1
(45) Date of Patent: Oct. 31, 2017

(54) PERSONALIZED PROSTHESIS AND METHODS OF USE

(71) Applicant: AneuMed, Inc., Los Altos, CA (US)

(72) Inventor: Hira V. Thapliyal, Los Altos, CA (US)

(73) Assignee: AneuMed, Inc., Los Altos, CA (US)

(*) Notice: Subject to any disclaimer, the term of this patent is extended or adjusted under 35 U.S.C. 154(b) by 0 days.

(21) Appl. No.: 15/628,444

(22) Filed: Jun. 20, 2017

Related U.S. Application Data

(60) Continuation of application No. 14/850,586, filed on Sep. 10, 2015, now Pat. No. 9,744,060, which is a
(Continued)

(51) Int. Cl.
*A61F 2/90* (2013.01)
*A61F 2/856* (2013.01)
(Continued)

(52) U.S. Cl.
CPC ............ *A61F 2/856* (2013.01); *A61F 2/0063* (2013.01); *A61F 2/07* (2013.01); *A61F 2/844* (2013.01); *A61F 2/848* (2013.01); *A61F 2/88* (2013.01); *A61F 2/90* (2013.01); *A61F 2002/061* (2013.01); *A61F 2002/072* (2013.01); *A61F 2002/075* (2013.01); *A61F 2210/0071* (2013.01); *A61F 2220/005* (2013.01); *A61F 2220/0008* (2013.01);
(Continued)

(58) Field of Classification Search
CPC ............... A61F 2/86; A61F 2/90; A61F 2/856
See application file for complete search history.

(56) References Cited

U.S. PATENT DOCUMENTS

| 4,436,684 A | 3/1984 | White |
|---|---|---|
| 5,116,365 A | 5/1992 | Hillstead |

(Continued)

FOREIGN PATENT DOCUMENTS

| CN | 1336160 A | 2/2002 |
|---|---|---|
| CN | 1421182 A | 6/2003 |

(Continued)

OTHER PUBLICATIONS

Co-pending U.S. Appl. No. 15/628,357, filed Jun. 20, 2017.
(Continued)

*Primary Examiner* — Christopher D Prone
*Assistant Examiner* — Suba Ganesan
(74) *Attorney, Agent, or Firm* — Wilson Sonsini Goodrich & Rosati

(57) ABSTRACT

A personalized prosthesis for implantation at a treatment site of a patient includes a self-expanding mesh or membrane having collapsed and expanded configurations. The collapsed configuration is adapted to be delivered to the treatment site, and the expanded configuration engages the personalized prosthesis with the treatment site. The mesh or membrane is personalized to match the treatment site in the expanded configuration, and has an outer surface that substantially matches the treatment site shape and size. The self-expanding mesh or membrane forms a central lumen configured to allow blood or other body fluids to flow therethrough. Methods of manufacturing and delivery of the personalized prosthesis are also disclosed.

19 Claims, 25 Drawing Sheets

Related U.S. Application Data division of application No. 13/663,160, filed on Oct. 29, 2012, now abandoned.

(60) Provisional application No. 61/554,099, filed on Nov. 1, 2011.

(51) Int. Cl.

| | | |
|---|---|---|
| *A61F 2/848* | (2013.01) | |
| *A61F 2/88* | (2006.01) | |
| *A61F 2/00* | (2006.01) | |
| *A61F 2/844* | (2013.01) | |
| *A61F 2/06* | (2013.01) | |
| *A61F 2/07* | (2013.01) | |

(52) U.S. Cl.
CPC .......... *A61F 2220/0016* (2013.01); *A61F 2220/0058* (2013.01); *A61F 2220/0075* (2013.01); *A61F 2240/001* (2013.01); *A61F 2240/002* (2013.01); *A61F 2240/004* (2013.01)

(56) References Cited

U.S. PATENT DOCUMENTS

| | | | |
|---|---|---|---|
| 6,165,193 A | 12/2000 | Greene, Jr. et al. | |
| 6,221,100 B1 | 4/2001 | Strecker | |
| 6,264,689 B1 * | 7/2001 | Colgan | A61F 2/90 623/1.22 |
| 6,383,216 B1 | 5/2002 | Kavteladze et al. | |
| 6,395,018 B1 | 5/2002 | Castaneda | |
| 6,500,190 B2 | 12/2002 | Greene et al. | |
| 6,695,833 B1 | 2/2004 | Frantzen | |
| 7,029,487 B2 | 4/2006 | Greene et al. | |
| 7,198,675 B2 | 4/2007 | Fox et al. | |
| 7,201,762 B2 | 4/2007 | Greene et al. | |
| 7,483,558 B2 | 1/2009 | Greene, Jr. et al. | |
| 7,769,603 B2 | 8/2010 | Jung et al. | |
| 7,799,047 B2 | 9/2010 | Greene, Jr. et al. | |
| 8,361,137 B2 | 1/2013 | Perouse | |
| 2002/0022875 A1 | 2/2002 | Strecker | |
| 2002/0055771 A1 | 5/2002 | Sandock | |
| 2004/0079737 A1 | 4/2004 | Pinchasik | |
| 2006/0058638 A1 | 3/2006 | Boese et al. | |
| 2007/0043432 A1 | 2/2007 | Perouse | |
| 2007/0293936 A1 | 12/2007 | Dobak, III | |
| 2008/0039923 A1 | 2/2008 | Taylor et al. | |
| 2008/0228216 A1 | 9/2008 | Strauss et al. | |
| 2009/0248131 A1 | 10/2009 | Greenan | |
| 2009/0309273 A1 | 12/2009 | Parker | |
| 2010/0114296 A1 | 5/2010 | Case et al. | |
| 2010/0185270 A1 | 7/2010 | Ramzipoor et al. | |
| 2010/0198333 A1 | 8/2010 | Macatangay et al. | |
| 2010/0274340 A1 | 10/2010 | Hartley et al. | |
| 2011/0016690 A1 | 1/2011 | Narainasamy et al. | |
| 2011/0313503 A1 | 12/2011 | Berra et al. | |
| 2013/0289690 A1 | 10/2013 | Thapliyal | |
| 2015/0374518 A1 | 12/2015 | Thapliyal | |

FOREIGN PATENT DOCUMENTS

| | | |
|---|---|---|
| CN | 1669538 A | 9/2005 |
| CN | 101332133 A | 12/2008 |
| CN | 101972181 A | 2/2011 |
| EP | 1057459 A1 | 12/2000 |
| EP | 1177779 A2 | 2/2002 |
| FR | 2858208 A1 | 2/2005 |
| JP | 2002035135 A | 2/2002 |
| JP | 2002132934 A | 5/2002 |
| JP | 2005514988 A | 5/2005 |
| JP | 2010528681 A | 8/2010 |
| JP | 2011516156 A | 5/2011 |
| WO | WO-9209246 A1 | 6/1992 |
| WO | WO-2004022150 A1 | 3/2004 |

OTHER PUBLICATIONS

Co-pending U.S. Appl. No. 15/628,431, filed Jun. 20, 2017.
European search report and search opinion dated Aug. 20, 2015 for EP Application No. 12845551.6.
International search report and written opinion dated Mar. 8, 2013 for PCT Application No. PCT/US2012/062595.
Notice of allowance dated May 10, 2017 for U.S. Appl. No. 14/850,586.
Office action dated Jun. 10, 2015 for U.S. Appl. No. 13/663,160.
Office action dated Jun. 13, 2014 for U.S. Appl. No. 13/663,160.
Office Action dated Aug. 26, 2016 for U.S. Appl. No. 14/850,586.
Office action dated Nov. 3, 2014 for U.S. Appl. No. 13/663,160.
PSI—Patient Specific Implants. Synthes CMF. Jul. 11, 2011. Retrieved on Feb. 26, 2013. http://www.synthes.com/MediaBin/US%20DATA/Product%20Support%20Materials/Brochures/CMF/MXBROPSI-J5245G.pdf.

* cited by examiner

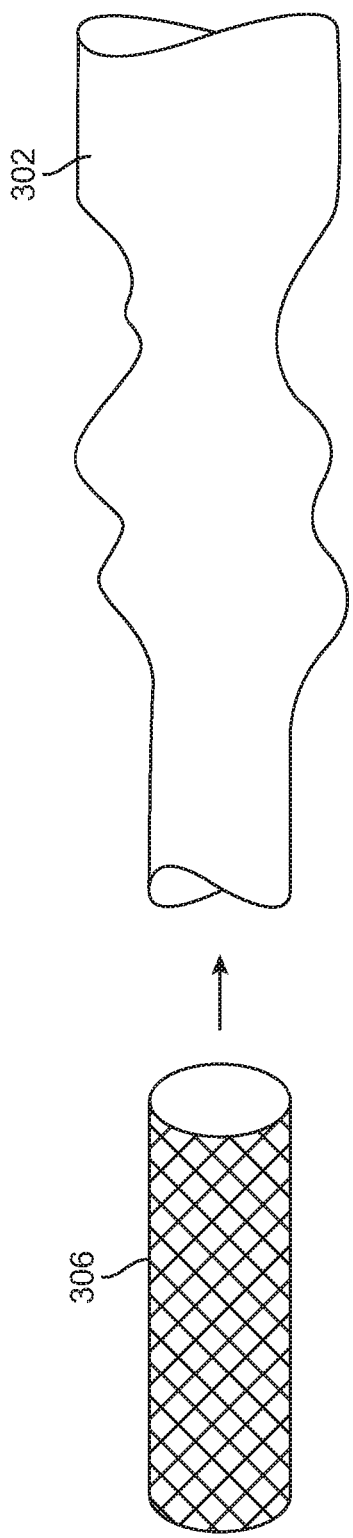

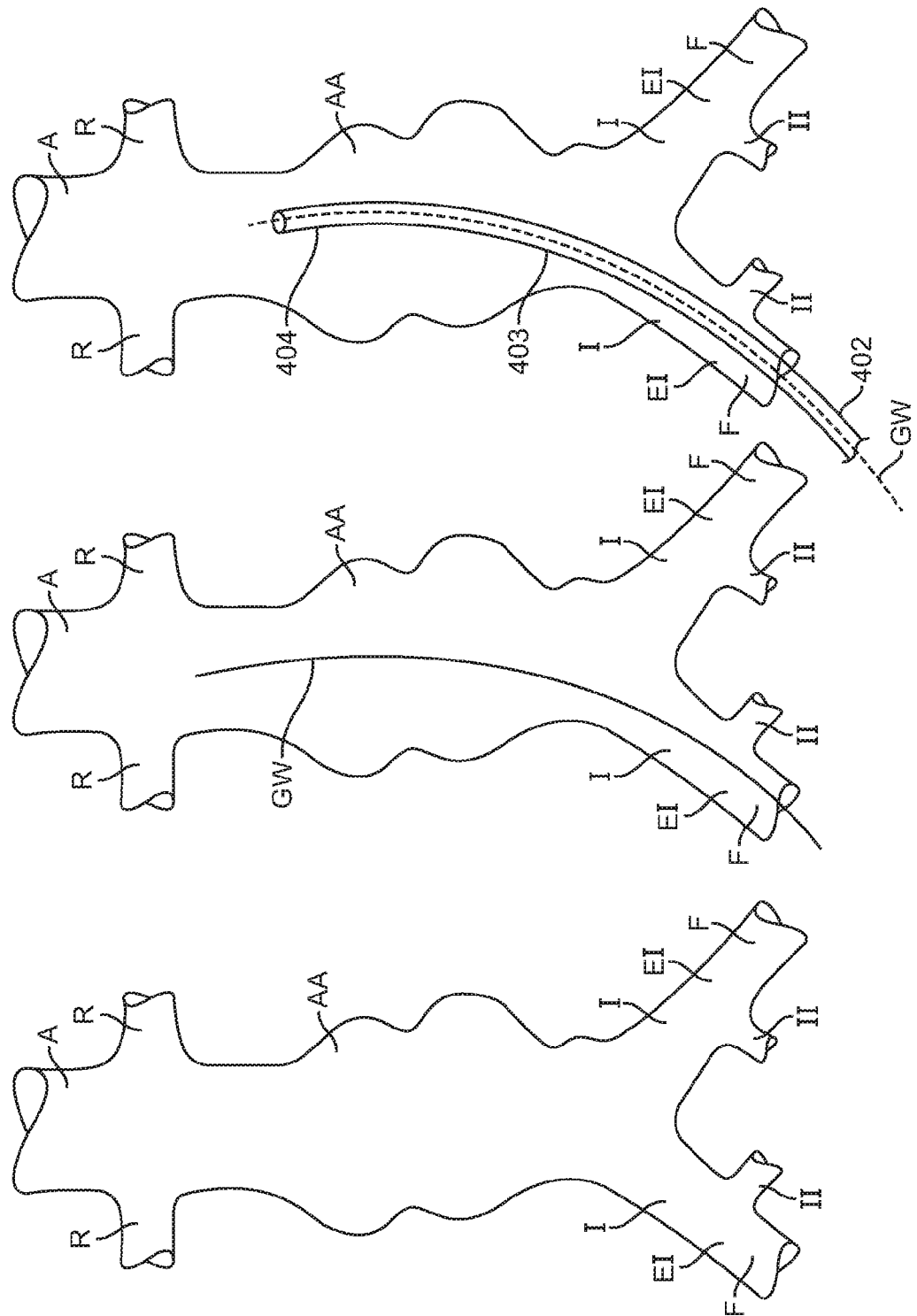

VIEW B-B

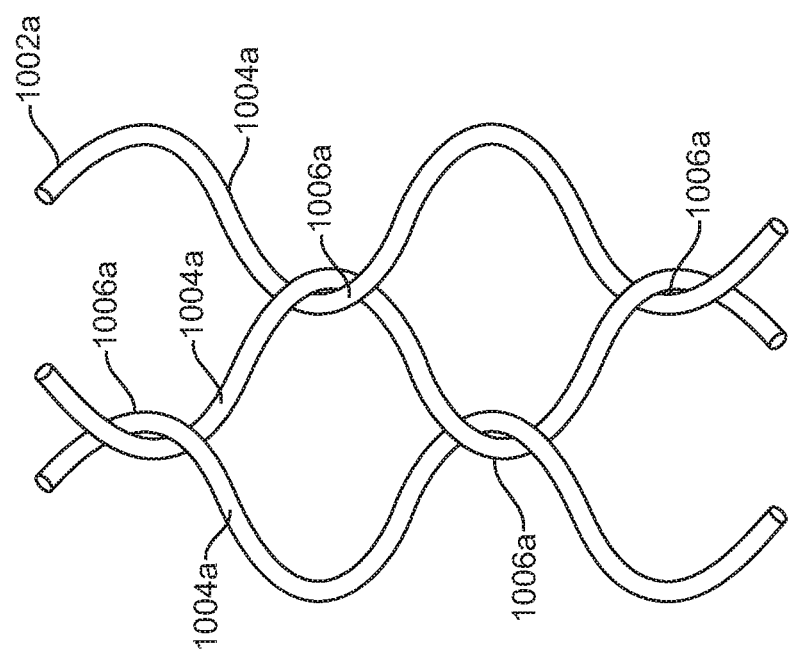

PERSONALIZED PROSTHESIS AND METHODS OF USE

CROSS-REFERENCE

The present application is a continuation of U.S. patent application Ser. No. 14/850,586 now U.S. Pat. No. 9,744,060 filed Sep. 10, 2015 which is a divisional application of U.S. patent application Ser. No. 13/663,160 filed Oct. 29, 2012 now abandoned, which is a non-provisional of and claims the benefit of U.S. Provisional Patent Application No. 61/554,099 filed Nov. 1, 2011; the entire contents of which are incorporated herein by reference.

BACKGROUND OF THE INVENTION

1. Field of the Invention

The present application generally relates to medical prostheses, methods for fabricating the prostheses, and methods for treating diseased or damaged tissue. More specifically, the present application relates to treatment of blood vessels or other body lumens and body cavities, including aneurysms such as in the aorta or in the brain.

An aneurysm is the localized dilation of a blood vessel which presents a serious medical condition. Such distention is the result of localized weakening of the vessel often caused by atherosclerosis, infection, or congenital defects. Most commonly aneurysms occur in arteries at the base of the brain or in the aorta. Cases of significant distention risk the possibility of vessel rupture and the resulting internal hemorrhage is a life threatening medical emergency that requires immediate surgical intervention. Aneurysms that are large enough to present an unacceptable level of risk of rupture are treated with preemptive surgery.

The most reliable surgical remedy for aneurysms is excision of the aneurysm and repair of the afflicted blood vessel with a graft. However, this procedure requires highly invasive surgery and often requires clamping of a major vessel such as the aorta, which can place a large strain on the patient's heart. Patients requiring aneurysm treatment often have co-morbid risk factors such as diabetes, heart disease, and hypertension, and thus such patients can be poor candidates for such a stressful operation. Accordingly, newer endovascular grafting methods for minimally invasive intervention of aneurysms are favored over traditional grafts for some patients. These endovascular installed grafts or "endoluminal grafts" are installed by accessing the aneurysm through the iliac arteries and have stent-like scaffolding supports at its terminal ends. Endoluminal grafts, however, in some situations are more prone to post-operative complications than traditionally installed grafts. Within two years of installation, a significant number of aortic endoluminal grafts exhibit leakage at the proximal interface to the aorta, necessitating further endovascular surgical intervention. Additionally, a small portion of endoluminal grafts drift inside the repaired blood vessel and expose the aneurysm. Repair of a drifted graft requires open surgery in a patient who is likely a poor candidate for such a procedure.

Endoluminal grafting must overcome geometrical problems stemming from morphological variations in aneurysm presentation and location. While most aneurysms are "fusiform," exhibiting distention along the entire circumference of the afflicted blood vessel, varied geometries exist. Some aneurysms display ballooning of the vessel on one side at a narrow neck (also referred to as saccular), or may have otherwise treacherous geometries. Other aneurysms may be located in close proximity to sensitive structures such as renal arteries. Endoluminal grafts in certain situations may encounter higher incidence of failure with non-fusiform geometries and may be unsuitable for implantation where the implants and their delivery techniques prove too incompatible or cumbersome for aneurysm geometry or location.

Given these concerns, there is strong unmet need for improved endoluminal grafts and delivery methods. Such an improved design preferably facilitates more reliable repair of aneurysms over a wider space of geometries and the ability to be delivered with such finesse as to shorten procedure time and expand the number of aneurysms that are treatable endovascularly. It would also be desirable if such improved endoluminal grafts also fit the patient's anatomy more accurately and therefore help prevent endoleaks and more securely anchor the endograft in the aneurysm and prevent drifting. At least some of these objectives will be met by the devices described herein.

2. Description of Background Art

Patents and Publications related to personalizable implants include but are not limited to U.S. Pat. Nos. 7,799,047; 7,769,603; 7,483,558; 7,201,762; 7,029,487; 6,500,190; 6,165,193; 4,436,684; and U.S. Patent Publication Nos. 2011/0016690; 2008/0228216; 2008/0039923; and 2006/0058638.

SUMMARY OF THE INVENTION

The present application generally relates to medical prostheses, methods for manufacturing the prostheses, and methods for treating diseased or damaged tissue. More specifically, the present application relates to treatment of blood vessels or other body lumens and body cavities, including aneurysms such as in the aorta, other arteries, or in the brain arteries. The techniques disclosed herein generally result in a personalized prosthesis that is designed and manufactured to match the anatomy of the patient's diseased or damaged tissue. The personalized prostheses may be commercially distributed once appropriate regulatory approvals have been obtained (e.g. Food and Drug Administration), and are not necessarily the same as "custom devices" defined in 21 CFR §812.3(b), which applies to non-commercial distribution of medical devices under certain circumstances, such as compassionate use.

The prostheses disclosed herein, such as mesh alone, covered mesh, or membrane alone may be implanted into a treatment site such as an aneurysm to stabilize the aneurysm and to help prevent it from growing larger. This applies to incipient aneurysms (e.g. untreated early stage aneurysms usually less than 50 mm in diameter) or larger, later stage aneurysms may also be treated using the prostheses described herein.

In a first aspect of the present invention, a method for manufacturing a personalized implantable prosthesis in a manufacturing facility comprises providing one or more images of a treatment site in a patient and creating a digital data set characterizing shape and volume of the treatment site based on the one or more images. The method also comprises transforming the digital data set into machining or fabrication instructions, and forming a mandrel using the machining or fabrication instructions. The mandrel has a shape that substantially matches the treatment site shape. The method further comprises applying a mesh to the mandrel, heat treating the mesh while the mesh is disposed over the mandrel so that the mesh is biased to return to a shape matching the shape of the treatment site, and optionally forming a membrane over the mesh thereby forming the personalized implantable prosthesis. The personalized implantable prosthesis has a contracted configuration and an expanded configuration. The personalized implantable prosthesis is adapted to be delivered to the treatment site in the contracted configuration, and the personalized implantable prosthesis is biased to return to the expanded configuration. The expanded configuration has a shape substantially matching or conforming to the treatment site shape and volume. Once the expanded personalized prosthesis is deployed at the treatment site, it may be anchored into the tissue and may provide support to the tissue. In the case of an aneurysm, the prosthesis prevents further expansion of the walls of the aneurysm.

Providing the one or more images may comprise providing one or more computerized tomography (CT) images, one or more magnetic resonance images (MRI), one or more x-ray images, one or more ultrasound images, or one or more an angiography images of the treatment site. Transforming the digital data set into machining instructions may comprise transferring the digital data set into a computer automated design/computer aided manufacturing (CAD/CAM) system. Forming the mandrel may comprise machining a piece of metal which may be undersized relative to the treatment site. The undersized mandrel may accommodate for thickness of the mesh and/or the membrane disposed thereover.

Applying the mesh to the mandrel may comprise slidably disposing a mesh over the mandrel, or wrapping a filament around the mandrel. The mesh may also be a preformed flat mesh which is wrapped around the mandrel with the ends of the mesh affixed to one another. Heat treating the mesh may comprise heat treating a nitinol mesh. The mandrel may be removed from the mesh so that the mesh may be recovered. At least one side aperture may be formed in the prosthesis, and the at least one side aperture may be configured to be aligned with a side branch vessel in the treatment site. Forming the membrane may comprise attaching a polymer cover to the mesh, or dip coating a polymer cover over the mesh thereby creating a personalized implantable prosthesis. The membrane may be biodegradable. The implantable prosthesis preferably is removed from the mandrel thereby forming a central lumen which extends through the prosthesis. The mandrel may be removed from the mesh and then the mesh may be recovered for further processing. In other embodiments, a cover may be applied directly over the mandrel to form the prosthesis with or without a mesh layer. The cover may be a polymer (e.g. expanded polytetrafluoroethylene), a fabric (e.g. Dacron), or other materials known in the art.

The method may further comprise the steps of mounting the implantable prosthesis on a delivery catheter, cleaning the implantable prosthesis and delivery catheter, packaging the implantable prosthesis, and terminally sterilizing the implantable prosthesis. The prosthesis mounted on the delivery system may then be shipped from the manufacturing facility to a hospital or other location. The method may also comprise mounting the personalized implantable prosthesis on a delivery catheter, placing the personalized implantable prosthesis and the delivery catheter in packaging, sterilizing the prosthesis and delivery catheter in the packaging, and requesting verification that the personalized implantable prosthesis is appropriate for implantation at the treatment site before shipping the personalized implantable prosthesis from the manufacturing facility. Verification may also occur prior to opening the sterile packaging holding the personalized implantable prosthesis. Verification may be performed by a physician, and may be performed over the Internet. The method may further comprise forming at least one side aperture in the personalized implantable prosthesis which can be aligned with a side branch vessel in the treatment site. The treatment site may be an aneurysm.

In another aspect of the present invention, a personalized prosthesis for implantation at a treatment site comprises a self-expanding mesh having a collapsed configuration and an expanded configuration. The collapsed configuration is adapted to be delivered to the treatment site, and the expanded configuration is adapted to expand the personalized prosthesis into engagement with the treatment site. The mesh in the expanded configuration is personalized to conform to or otherwise match the treatment site. The mesh has an outer surface that substantially matches the treatment site shape and size in the expanded configuration, and the self-expanding mesh forms a central lumen that is configured to allow blood or other body fluids to pass therethrough.

The self-expanding mesh may comprise a nitinol mesh, or it may comprise one or more filaments in a helical pattern. The mesh may also comprise barbs or hooks adapted to engage tissue at the treatment site and anchor the prosthesis. The mesh may also comprise a plurality of overlapping filaments forming twisted or overlapping regions. The overlapping regions form raised surfaces that may be adapted to engage tissue at the treatment site and anchor the prosthesis. The one or more filaments may be woven together to form overlapping regions with the filaments overlapping one another at least once, twice, three times, or more. In other embodiments, some of the overlapping regions may have a first number of overlaps of the filaments while in other overlapping regions there may be a second number of overlaps different than the first number.

The prosthesis may also comprise a biodegradable or non-biodegradable membrane disposed over the mesh. The membrane may be elastic and may conform to the self-expanding mesh. The membrane may have an outer surface that substantially matches the treatment site shape in the expanded configuration. The membrane may form a central lumen configured to allow blood or other body fluids to pass therethrough. The treatment site may have a shape, and the lumen may have a shape that substantially matches the shape of the treatment site. Thus, the lumen may not substantially alter blood flow across the treatment site. In some embodiments, the lumen may have a substantially cylindrical shape. The cylindrically shaped lumen may be formed from an invaginted portion of the personalized prosthesis. The membrane may comprise a resilient polymer, and the polymer may be impermeable to blood. The membrane may also comprise an elongated neck portion, and invagiation of the elongated neck into the personalized prosthesis forms the central lumen. The prosthesis may also comprise one or more radiopaque markers coupled to the membrane or the self-expanding mesh for facilitating implantation of the prosthesis at the treatment site. The prosthesis may also comprise one or more apertures extending through a sidewall of the prosthesis. The one or more apertures may be fluidly coupled with the central lumen to allow blood flow or other fluids to flow between the central lumen and the one or more apertures. The one or more apertures may be configured to accommodate side branch vessels or other body passages such that the prosthesis does not obstruct blood flow or fluid flow therethrough. The prosthesis may also include a plurality of barbs coupled to either the mesh or the membrane, and the barbs may be adapted to anchor the personalized prosthesis to the treatment site. The prosthesis may have an end that is flared radially outward to engage tissue and help anchoring.

In yet another aspect of the present invention, a personalized prosthesis for implantation at a treatment site in a patient may comprise a self expanding membrane having a collapsed configuration and an expanded configuration. The collapsed configuration is adapted to be delivered to the treatment site, and the expanded configuration is adapted to expand the personalized prosthesis into engagement with the treatment site. In the expanded configuration the membrane is personalized to match the treatment site and has an outer surface that substantially matches the treatment site shape and size. The membrane forms a central lumen configured to allow blood or other body fluids to pass therethrough.

In another aspect of the present invention, a method for treating damaged or diseased tissue at a treatment site comprises providing an implantable prosthesis having a central lumen, an expanded configuration and a collapsed configuration. The implantable prosthesis is biased to expand into the expanded configuration, and the implantable prosthesis is personalized to match shape of the treatment site. The central lumen is configured to allow blood flow or other body fluids to pass therethrough. The method also comprises advancing the implantable prosthesis in the collapsed configuration to the treatment site, and self-expanding the implantable prosthesis into the expanded configuration. In the expanded configuration the implantable prosthesis has a shape that substantially matches the shape of the treatment site such that the implantable prosthesis expands substantially into engagement with tissue at the treatment site. The prosthesis then reinforces the tissue.

The implantable prosthesis may comprise a resilient polymer or a self-expanding wire mesh, and the mesh may be surrounded by a polymer cover. The treatment site has a shape, and the lumen created by the prosthesis may have a shape that substantially matches the shape of the treatment site. The lumen may also be cylindrically shaped, and the lumen may be disposed inside the implantable prosthesis. The lumen may not substantially alter blood flow path across the treatment site. Advancing the implantable prosthesis may comprise advancing the implantable prosthesis through a blood vessel. Radially expanding the implantable prosthesis may comprise retracting a sheath away from the implantable prosthesis, thereby allowing the implantable prosthesis to self-expand into the expanded configuration.

Reinforcing the tissue may comprise anchoring the implantable prosthesis to the tissue. The treatment site may comprise an aneurysm, and reinforcing the tissue may comprise preventing the aneurysm from enlarging. The aneurysm may also be excluded by the prosthesis, and the prosthesis may be anchored with the tissue. Anchoring the prosthesis may comprise engaging barbs on the implantable prosthesis with the tissue. Reinforcing the tissue may comprise constraining the tissue from moving radially outward or radially inward.

The method may optionally include aligning one or more radiopaque markers on a delivery device or on the prosthesis with one or more anatomical features at the treatment site. The implantable prosthesis may comprise one or more apertures in a sidewall of the prosthesis, and the method may comprise aligning the one or more apertures with one or more corresponding side branch vessels or body passages at the treatment site. This prevents obstruction of the one or more side branch vessels or the body passages. The implantable prosthesis may be sealed against the tissue at the treatment site to prevent blood flow therepast.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A-3H illustrate exemplary methods of fabricating a personal prosthesis for treatment of an aneurysm.

FIGS. 4A-4F illustrate an exemplary method of delivering a personal prosthesis to a treatment site.

FIGS. 12A-12F illustrates exemplary mesh patterns.

DETAILED DESCRIPTION OF THE INVENTION

The present invention will be described in relation to an abdominal aortic aneurysm. However, one of skill in the art will appreciate that this is not intended to be limiting, and the devices and methods disclosed herein may be used in aneurysms in other parts of the body such as in the brain, as well as used to treat other hollow anatomical structures including ducts, vessels, organs, or any other part of the body where there is a need to reinforce a lumen, channel or other body space. For example, a personalized prosthesis may be fabricated using the techniques described herein for implantation in or around the bladder in order to treat incontinence, or the prosthesis may be personalized to treat a diseased or damaged pyloric valve in the stomach, or other body passages such as a biliary duct.

Figure 1A:
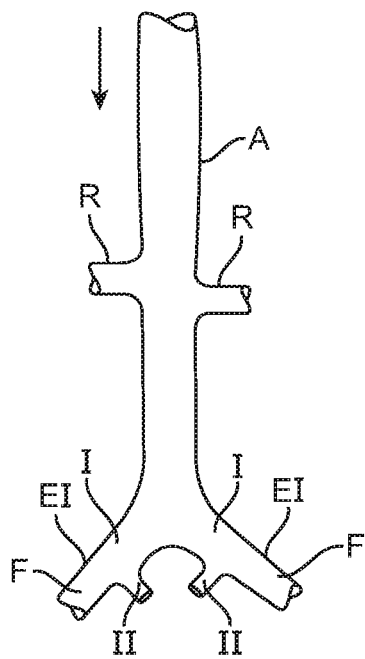
FIG. 1A illustrates a normal abdominal aorta.

FIG. 1A illustrates typical anatomy in a normal section of the abdominal aorta A where blood flows downstream as indicated by the arrow from the heart toward the legs. The aorta is typically a gradually tapering cylinder. A pair of renal arteries R branch off laterally from the aorta A and provide blood to the kidneys (not shown). The aorta bifurcates into two common iliac arteries I which then further bifurcate into the external iliac artery EI and the internal iliac artery II. After the external iliac arteries EI pass the inguinal ligament (not shown) they are then generally referred to as the femoral arteries F. Thus, the aorta provides for smooth blood flow from the heart to the lower extremities of the body.

Figure 1B:
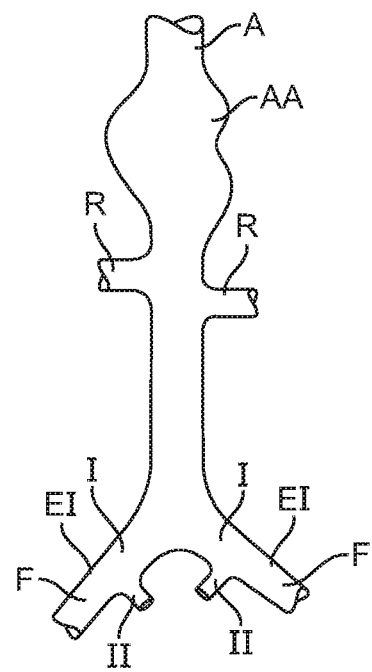
FIGS. 1B-1D illustrate various abdominal aortic aneurysms.
Figure 1C:
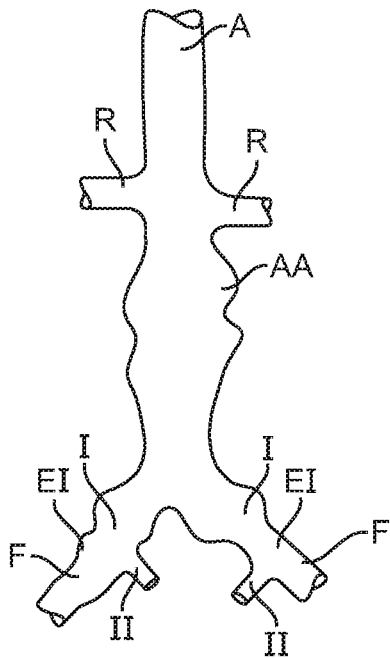
Figure 1D:
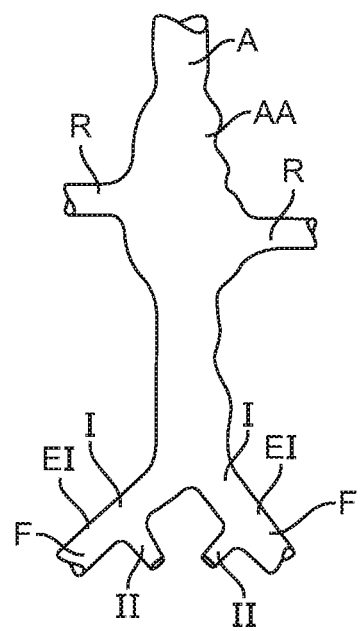
Figure 1E:
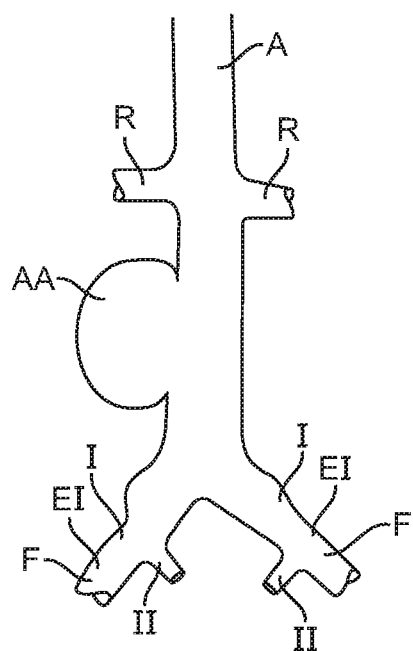
FIG. 1E illustrates a saccular aneurysm.

However, in some cases, the tissue in the aorta may become weakened due to disease or damage thereby resulting in a bulged region known as an aneurysm. The aneurysm may be at any point along the abdominal aorta. For example, FIG. 1B illustrates a suprarenal aortic aneurysm where the aneurysm AA is superior to (or upstream or above) the renal arteries R. FIG. 1C illustrates an infrarenal aneurysm AA which is inferior to (or downstream or just below) the renal arteries and this type of aneurysm represents the majority of abdominal aortic aneurysms. FIG. 1C also illustrates that the aneurysm does not always remain strictly in the aorta, and that the aneurysm may extend into the iliac arteries and femoral arteries. FIG. 1D illustrates a juxtarenal aortic aneurysm AA where the aneurysm extends over the portion of the aorta from which the renal arteries branch off. Each of the aneurysms illustrated in FIGS. 1B-1D are referred to as fusiform aneurysms in which the weakened aorta and resulting bulge extend essentially all the way around the vessel. However, aneurysms may also be saccular in which only a portion of the vessel wall bulges outward, such as in FIG. 1E.

As discussed above, standard surgical procedures for aneurysm repair use a natural graft or an artificial graft typically made of Dacron™ polyester or expanded polytetrafluorinated ethylene (ePTFE) to replace the damaged or diseased section of the vessel. This procedure is highly invasive, can result in a number of post-operative complications, and requires a lengthy recovery period. More recently, minimally invasive endovascular repair techniques have been developed in which a stent-graft is delivered to the treatment site. The stent-graft is then radially expanded into the aneurysm thereby forming a new lumen for blood flow that excludes the aneurysm. While stent-grafts are promising, the implanted device may obstruct blood flow to side branch vessels, or the implant may be pushed downstream away from the treatment site due to the force of the blood and its pulsating nature. This is sometimes referred to as "windsocking."

Additionally, stent-grafts do not always seal perfectly against the vessel wall, thereby allowing blood to continue to pressurize the aneurysm sac. Endoleaks are a major cause of failure in the treatment of aneurysms with stent-grafts. Endoleaks have been classified into several categories including Type I endoleaks where blood flows into the aneurysm sac due to incomplete sealing at the proximal end of the stent-graft. The proximal end as used herein with respect to the prosthesis, is the end closest to the heart, and the distal end of the prosthesis is the downstream end. When referring to a delivery system used to deliver a prosthesis, the proximal end of the delivery system is the end that is furthest away from the heart and usually closest to the operator, and the distal end is the closest to the heart and typically furthest away from the operator. Type II endoleaks result when blood flows into the aneurysm sac from collateral vessels. Type III endoleaks result in blood flow into the aneurysm sac due to poor sealing between stent-graft joints or rupture of the stent-graft. Type IV endoleaks result in blood flow into the aneurysm sac due to excessive or unwanted porosity in the stent-graft that permits blood to flow through the stent-graft into the aneurysm. Endoleaks may result from improper fitting or matching of the stent-graft to the patient's anatomy.

Thus it is clear that there is a need for a prosthesis that can be used to treat aneurysms that has better anchoring to prevent windsocking and that fits the aneurysm anatomy more accurately in order to minimize the possibility of endoleaks and that maintains blood flow to side branch vessels. A personalized prosthesis will address at least some of these issues. Current imaging systems can be linked with computer aided design (CAD) and computer aided manufacturing (CAM) systems to allow a prosthesis to be fabricated that matches the patient's anatomy.

Figure 2:
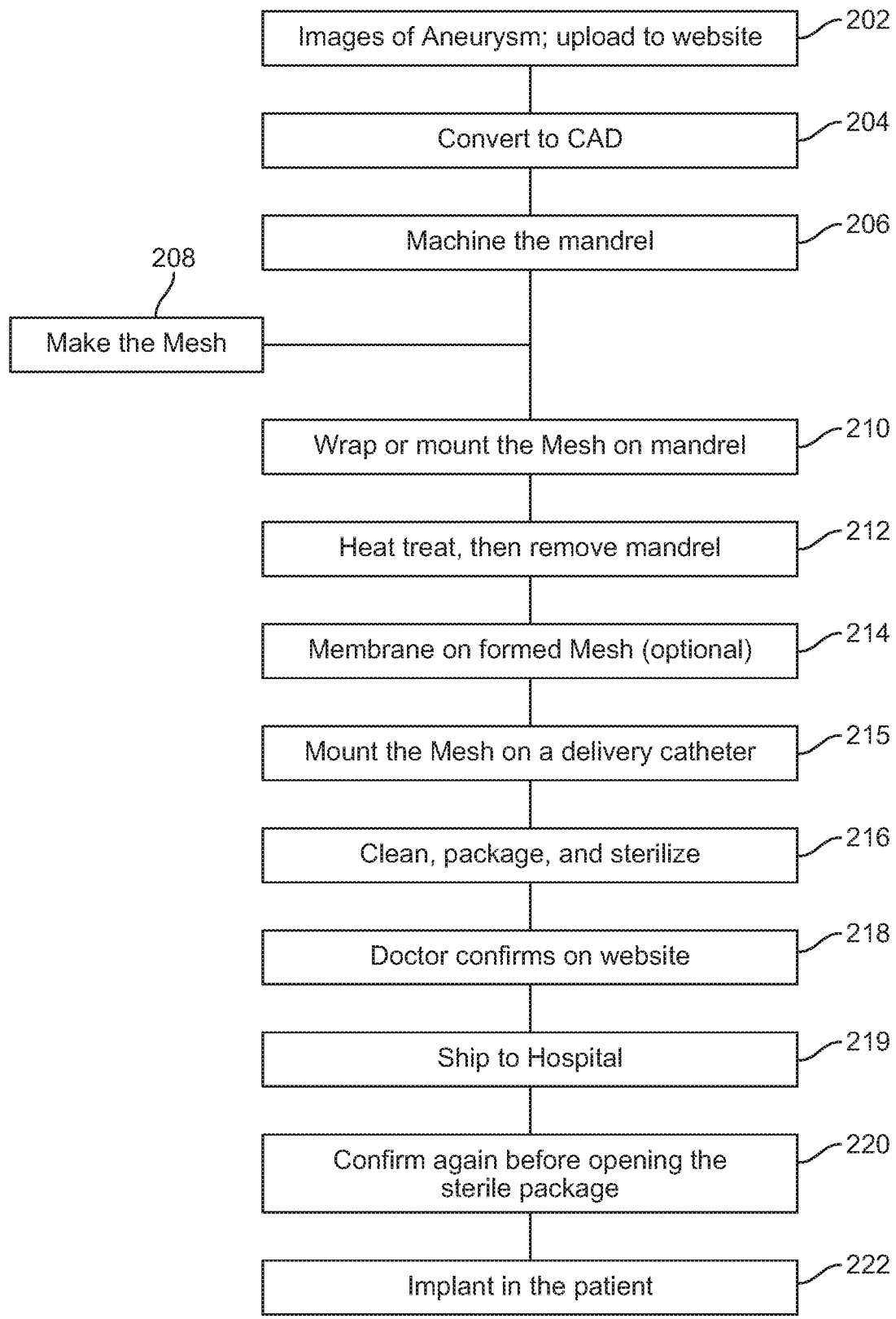
FIG. 2 illustrates a flow chart of an exemplary method of fabricating a personalized prosthesis.

FIG. 2 is a flow chart which illustrates an exemplary method of fabricating a personalized prosthesis that can be used to treat aneurysms or any other treatment region. The method includes obtaining one or more images 202 of the treatment region which in this case is an aneurysm. These images may be obtained using computerized tomography (CT), x-ray, angiography, magnetic resonance imaging (MRI), ultrasound, or other imaging techniques known to those of skill in the art. The images may be stored on any storage media such as a CD-rom, flash memory stick, etc., or the images may be stored in the cloud, on a remote server, or any other convenient and secure location. The images may be transferred to any of these locations using the Internet. Once the images are stored, the images or the digital data representing the images may be input 204 into a computer aided design/computer aided manufacturing (CAD/CAM) system. The CAD/CAM system then converts the images into a digital data set that can then be translated into machining instructions which are provided to a machining device such as a CNC lathe, mill, electrical discharge machine (EDM), etc. and the machining instructions are used by the machining device to machine 206 or otherwise form a mandrel or a mold having a shape that substantially matches the shape and volume of the treatment region. Thus the contours of the mandrel will match the contours of the treatment region, and the mandrel will substantially fill the volume of the treatment region, typically a body cavity, lumen, or other passage. The CAD/CAM system may be programmed to compensate for the thickness of materials that are applied to the mandrel later on, thus the mandrel may be slightly smaller than the actual size of the treatment region. In other embodiments, the mandrel shape will match the contours of the treatment region without compensating for material thickness. In both cases, the resulting mandrel shape substantially matches the treatment region shape and size, and the mandrel will substantially fill the volume of the treatment region. For example, in the case of an abdominal aortic aneurysm, the mandrel will substantially fill the volume of the aneurismal sac as well as a portion of the aneurysm neck and legs.

Once the mandrel is formed, it can be used as a master mold from which a personal prosthesis is fabricated. The personal prosthesis will then have a size and shape that substantially matches the treatment region which allows the personal prosthesis to anchor itself at the treatment region and prevent endoleaks and windsocking. A wire mesh is either pre-made 208 or otherwise provided. The mesh is preferably tubular and cylindrically shaped with both ends open so that the mesh may be slidably disposed over the mandrel like a sock, or in other embodiments the wire mesh may be wound 210 on the mandrel. The mesh and mandrel are then placed in a furnace, oven, salt bath, etc. to an elevated temperature for a desired time. The mesh and mandrel are then removed and cooled using a prescribed cooling procedure such as air cooling, quenching in oil or water, etc. This heat treats 212 the wire mesh and the wire mesh takes a set to the shape of the mandrel. Heat treating of metals, in particular self-expanding metals is known in the art. The formed mesh is then removed from the mandrel. In this embodiment, or any of the embodiments disclosed herein the wire mesh is preferably self-expanding, and may be made from metals such as superelastic nitinol, and thus the mesh will have an expanded configuration which matches the mandrel and hence also substantially matches the shape of the treatment region. When tension is applied to the ends of the mesh, the mesh will collapse into a collapsed configuration which has a lower profile and is suitable for loading onto a delivery catheter for endovascular delivery to the treatment region. The wire mesh in this or any of the embodiments described herein may also be a shape memory alloy such as nitinol such that placement of the mesh in a patient's body heats the mesh above a transition temperature and causes the mesh to radially expand outward. In still other embodiments, the mesh may be balloon expandable, so it may be delivered over an expandable member such as a balloon. When the balloon is expanded, the mesh similarly expands with the balloon.

Once the wire mesh has been heat treated, a fabric or polymer coating may be applied 214 to the wire mesh. The coating may be Dacron® polyester, expanded polytetrafluorinated ethylene (ePTFE), silicone, polyurethane, or other materials known in the art. The coating may be a sheet or tube of the material coupled to the mesh with adhesives, sutures, encapsulation, etc., or the mesh may be dip coated in order to apply the polymer to the mesh. The coating is preferably biocompatible and impermeable to blood or other body fluids. It may also be biodegradable and be made of materials such as polylactic acid (PLA) or polyglycolic acid (PGA). The resulting wire mesh with polymer coating forms a personalized implantable prosthesis having a shape that matches the treatment region and substantially fills the volume of the treatment region, in this case, the aneurismal sac. In other embodiments, the wire mesh remains uncoated and uncovered and forms the personalized prosthesis. The personalized implantable prosthesis is then coupled to a delivery system 215 such as a delivery catheter, and the system is then cleaned, packaged, and terminally sterilized 216 using manufacturing processes known to those of skill in the art. For example, packaging may comprise placing the prosthesis in a procedure tray and sealing the tray with a Tyvek® lid, and terminally sterilizing the prosthesis may comprise gassing the prosthesis with ethylene oxide, autoclaving it with steam, or irradiating it with gamma or electron beam irradiation. In alternative embodiments, the coating may be applied directly to the mandrel without the mesh, thereby forming the prosthesis.

In some embodiments, the physician optionally may then confirm 218 that the resulting personal prosthesis is indeed the correct one for a particular patient prior to shipping the prosthesis from the factory. The verification may be conducted visually over the Internet by verifying size, shape, or dimensions of the prosthesis. Once the verification is complete, the personal prosthesis may be shipped 219 from the manufacturing facility to the doctor at a hospital, surgicenter, clinic or other place of business. Once received, the doctor may then optionally re-verify 220 that the prosthesis is the correct size and shape for the patient prior to opening up the sterile package. If the prosthesis is incorrect, it may be returned to the manufacturing facility. Verification may be accomplished by scanning a bar code and/or using the Internet. Once verification is complete, the personal prosthesis may be implanted 222 in the appropriate patient. One of skill in the art will also appreciate that appropriate patient privacy must be maintained during the entire personalized manufacturing process as required by the Health Insurance Portability and Accountability Act (HIPAA). In an alternative embodiment, the mesh alone may be formed over the mandrel and then delivered as described herein to treat the diseased or damaged tissue. Similarly, in another alternative embodiment, a resilient polymer may be formed directly over the personalized mandrel without the mesh. This may then be used to treat the diseased or damaged tissue as described herein.

Figure 3B:
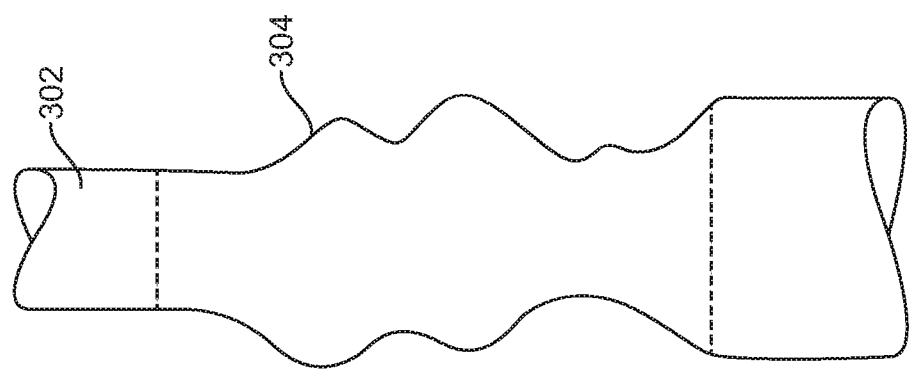
Figure 3A:
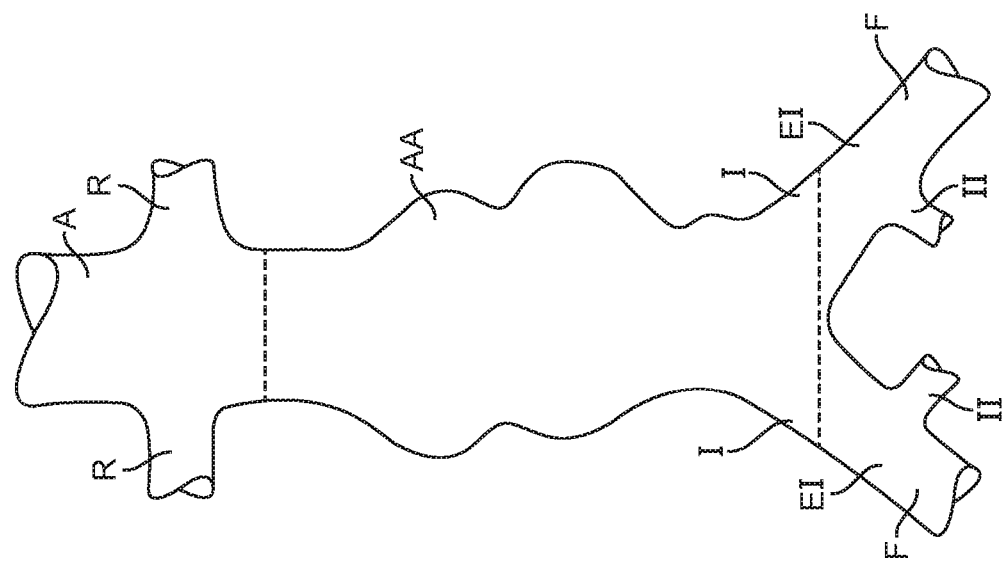
Figure 3F:
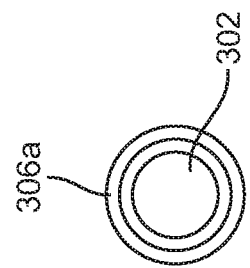
Figure 3E:
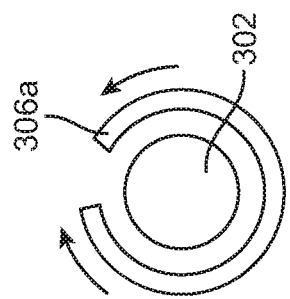
Figure 3D:
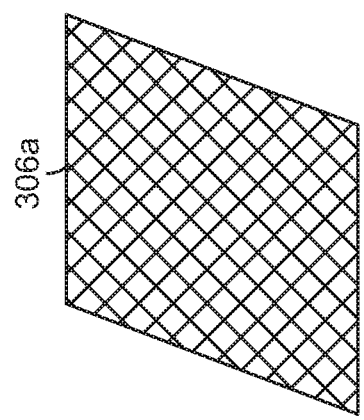
Figure 3I:
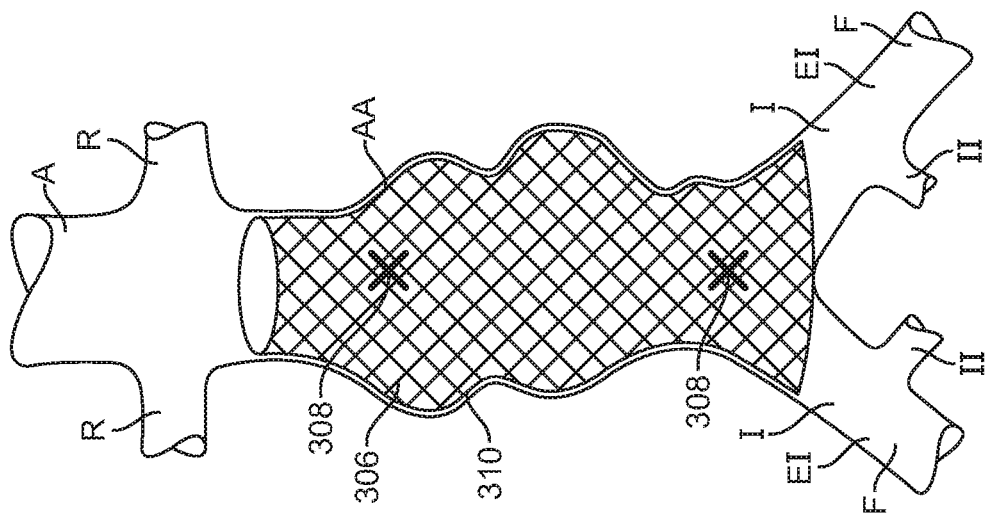
FIG. 3I illustrates the prosthesis fabricated in FIGS. 3A-3H deployed in an aneurysm.
Figure 3H:
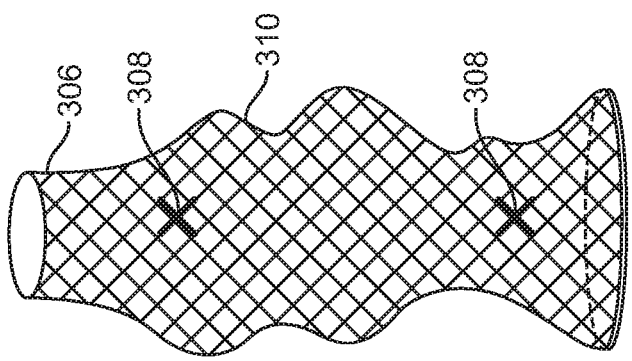
Figure 3G:
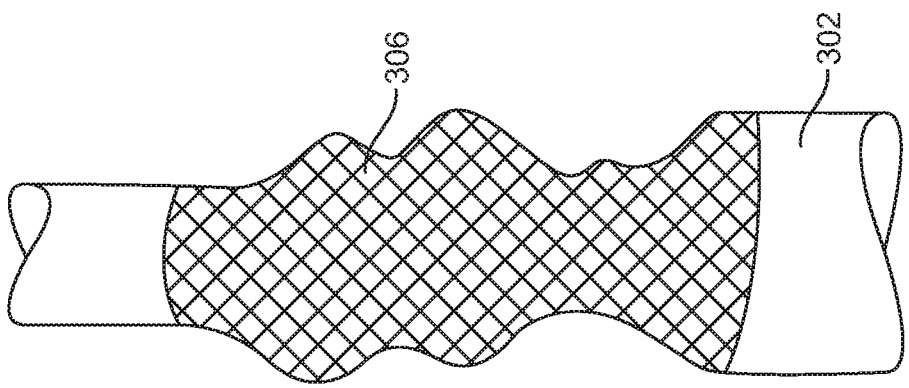

FIGS. 3A-3I illustrate exemplary methods of fabricating a personal prosthesis for treatment of an aneurysm. FIG. 3A illustrates an infrarenal aneurysm AA similar to that illustrated in FIG. 1C above. Using the fabrication technique described above, images of the aneurysm may be obtained using CT scans, or any of the other techniques described herein or known in the art. The image is then used to create a mandrel 302 having a surface 304 which substantially matches the contours of the inner wall of the aneurysm as shown in FIG. 3B. As described above, the mandrel may be made slightly undersized in order to accommodate for material thicknesses that are disposed on top of the mandrel. In some situations, the mandrel may be made oversized if needed. The mandrel may be made from stainless steel, aluminum, or any other material that resists the heat experienced during heat treatment. Once the mandrel is made, a wire mesh 306 may be disposed over the mandrel such that the mesh takes the shape of the mandrel and hence the mesh then also has a shape which substantially matches the shape of the aneurysm. The wire mesh 306 may be pre-fabricated into a tubular sock-like shape that can be easily placed over the mandrel as seen in FIG. 3C, or in other embodiments, the wire mesh may be wound and formed over the mandrel. In still other embodiments, such as seen in FIGS. 3D-3F, a flat preformed mesh 306a (best seen in FIG. 3D) may be wrapped around the mandrel 302 as seen in FIG. 3E. Once wrapped, the ends of the flat mesh may be affixed to one another using methods known in the art such as welding, suturing, tying, bonding, soldering, etc. The mesh is then circumferentially disposed around the mandrel as seen in FIG. 3F. A ribbon, wire, or other filament may be wrapped over the mesh to ensure that it contacts the mandrel. FIG. 3G illustrates the wire mesh disposed over the mandrel. The mandrel and mesh are then heat treated as described previously so that the wire mesh takes a set to the shape of the mandrel. The mesh is preferably nitinol and is self expanding, thus the mesh may be collapsed into a collapsed configuration for delivery, and the wire mesh may self-expand into an expanded shape which matches the mandrel and the aneurysm shape. After heat treatment is completed, the mesh and mandrel may be dip coated with a polymer, or the polymer or fabric cover 310 may be applied to the mesh using methods described above or known to those of skill in the art. The polymer or fabric cover 310 is preferably impermeable to blood to prevent blood from flowing across the wall of the prosthesis. Radiopaque markers 308 or other indicator markers are optionally attached to the polymer or fabric cover and/or to the wire mesh. The personal prosthesis is now complete and will substantially match the anatomy of the aneurysm. This allows the prosthesis to seat itself in the aneurysm thereby anchoring the prosthesis in position, and further excludes the aneurysm from blood flow, thereby preventing endoleaks. FIG. 3H illustrates the personal prosthesis with markers 308 once the mandrel has been removed. The device can then be loaded onto a delivery catheter or other delivery device and implanted at the site of the infrarenal aneurysm as seen in FIG. 3G. Additional details about prosthesis delivery and implantation are described below.

FIGS. 4A-4F illustrate an exemplary method of delivering a personalized prosthesis that is fabricated to match the patient's anatomy at the treatment site. The personalized prosthesis is preferably fabricated using the methods described herein. This exemplary method is directed at treatment of an aortic aneurysm, but could also be used to treat aneurysms in other parts of the body such as a cerebral aneurysm, or other body cavities such as a stomach, bladder, etc.

FIG. 4A illustrates an infrarenal aortic aneurysm AA in a portion of the aorta inferior to the renal arteries R. In this embodiment, the aneurysm does not extend into the iliac arteries I, external iliac arteries EI, internal iliac arteries II, or femoral arteries F. Thus, in this case the repair of the prosthesis does not need to extend past the aortic bifurcation into the iliac arteries I. However, in the situation where the diseased or damaged tissue extends past the aortic bifurcation, a similarly personalized prosthesis may be fabricated using similar methods described above. The prosthesis may be a single piece or it may be modular and assembled in situ. In FIG. 4B a standard guidewire GW is inserted by surgical cutdown or percutaneously (e.g. using the Seldinger technique) into a femoral artery and then advanced so that the distal tip of the guidewire is positioned beyond the location of the aneurysm.

Figure 4F:
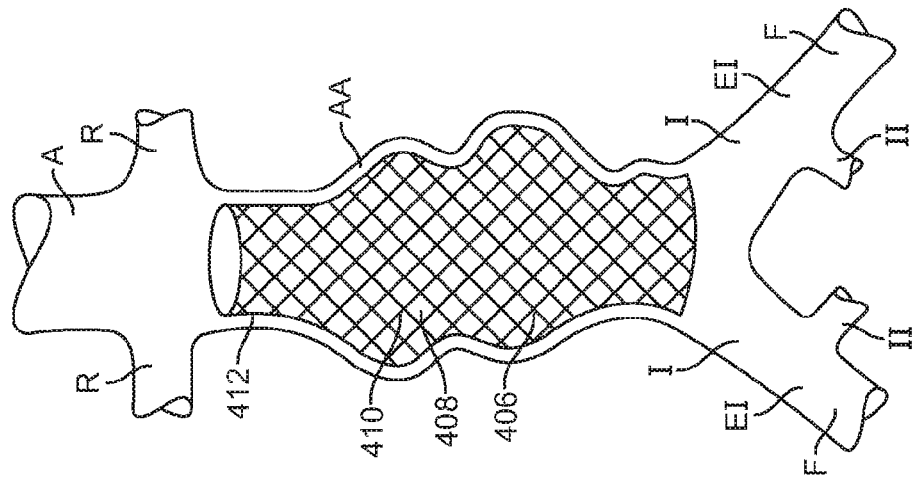
Figure 4E:
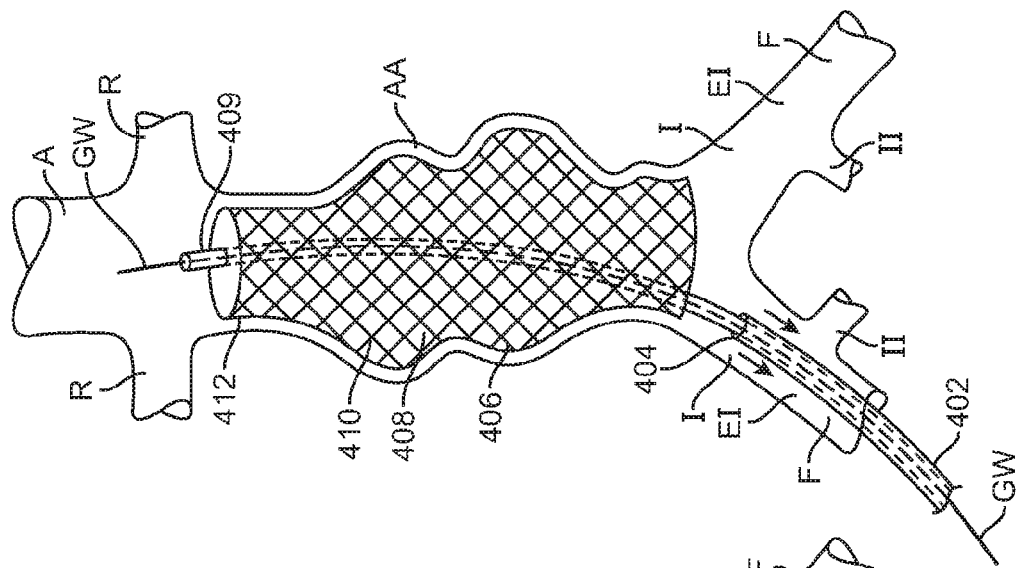
Figure 4D:
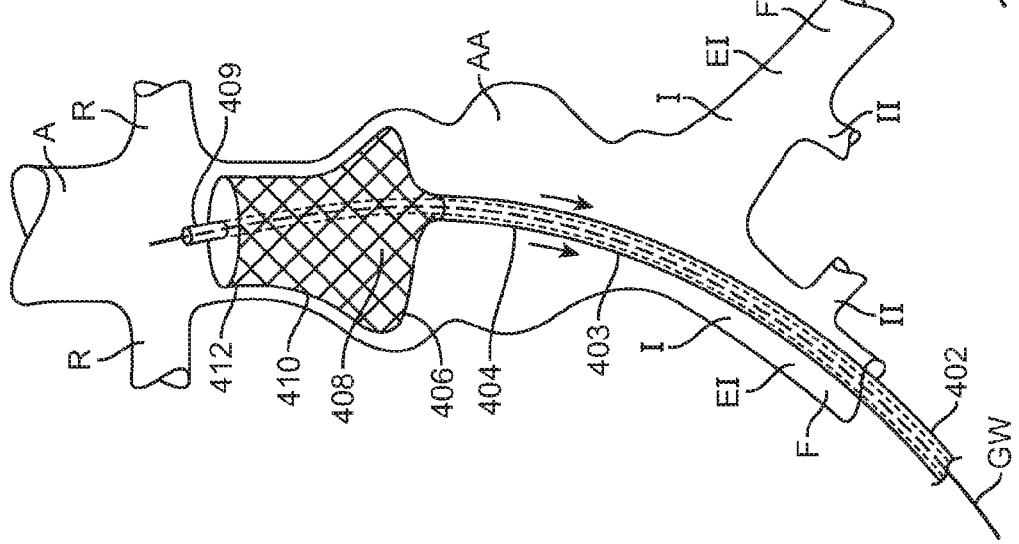

A delivery device such as a catheter 402 carrying the prosthesis can then be advanced over the guidewire GW so that the distal portion 404 of the delivery catheter 402 is positioned beyond the location of the aneurysm and preferably is upstream or superior to the proximal end (closest to the heart) of the aneurysm, as illustrated in FIG. 4C. Now referring to FIG. 4D, the delivery device may include an inner shaft 409 which carries the prosthesis 406, and an outer sheath 403 which constrains the prosthesis from expansion during delivery. The delivery device may have radiopaque markers (not shown) or other indicators to facilitate visualization, alignment, and delivery, or optional radiopaque markers or other indicators on the prosthesis itself may be used to help position the device. Once the delivery catheter is appropriately positioned relative to the aneurysm, the outer sheath 403 may be retracted proximally (toward the physician operator) to expose the personalized prosthesis 406 having a mesh 408 and polymer cover 410. When referring to the catheter, the term proximally refers to a position closest to the physician operating the catheter, and distal refers to a position furthest away from the physician operating the catheter. When referring to the aneurysm or the prosthesis, a proximal portion of the aneurysm or prosthesis is the portion closest to the heart (also referred to as upstream), and the distal portion of the aneurysm or prosthesis is furthest away from the heart (also referred to as downstream). The prosthesis 406 is a personalized prosthesis that has been manufactured to match the anatomy of the treatment site using the methods described herein. The prosthesis 406 may be any of the embodiments of prostheses described herein. Retraction of the outer sheath 403 as indicated by the arrows in FIG. 4D removes the constraint from the prosthesis 406 thereby allowing the prosthesis to self-expand into engagement with the walls of the aorta upstream of the aneurysm. Thus, an upstream portion 412 of the prosthesis 406 radially expands outward into engagement with the aneurysm. The outer sheath 403 is further retracted until as indicated by the arrows in FIG. 4E until the entire prosthesis 406 is free of a constraint, and thus the prosthesis 406 radially expands into engagement with the walls of the aneurysm and preferably above and below the aneurismal sac as well. Once the prosthesis has been delivered, the delivery catheter and guidewire may be removed from the patient leaving only the prosthesis 406 behind, as seen in FIG. 4F. Because the prosthesis 406 has been personalized to match the contours of the aneurysm, the prosthesis will expand to substantially fill the entire aneurismal sac and the prosthesis will engage the walls of the aneurysm over the entire treatment region.

Filling the entire sac and having engagement of the prosthesis with the walls of substantially all of the aneurysm securely anchors the prosthesis in position thereby preventing migration, and also ensures good sealing between the prosthesis and the vessel. This prevents endoleaks and thus excludes the aneurysm from blood flow, thereby alleviating pressure on the weakened walls of the aneurysm which prevents further dilation. Thus the personalized prosthesis reinforces the aneurysm. Additionally, in some aneurysms there may be mural thrombus on the walls of the aneurysm. Implanting a personalized prosthesis that matches the contours of the aneurysm helps to trap any mural thrombus between the prosthesis and the aneurismal wall, thereby preventing the mural thrombus from embolizing. Additionally, endothelial cells will cover the prosthesis and further facilitate anchoring of the device in position. Endothelialization begins about two weeks after implantation, and is substantially complete after approximately two months. The prosthesis in FIGS. 4A-4F reinforce the walls of the aneurysm and alleviates the pressure from blood flow through the aneurysm, thereby preventing the aneurysm from further dilation. No new lumen is created in this embodiment, the blood flows through a path that is substantially similar to its original path and that no longer contacts the wall of the aneurysm due to the walls of the personalized prosthesis. However, in some circumstances, it may be beneficial to create a new lumen for blood flow. The new lumen may further prevent exertion of blood pressure against the walls of the aneurysm, or may restore natural blood flow or hemodynamics back to, or close to pre-aneurismal conditions.

Figure 5A:
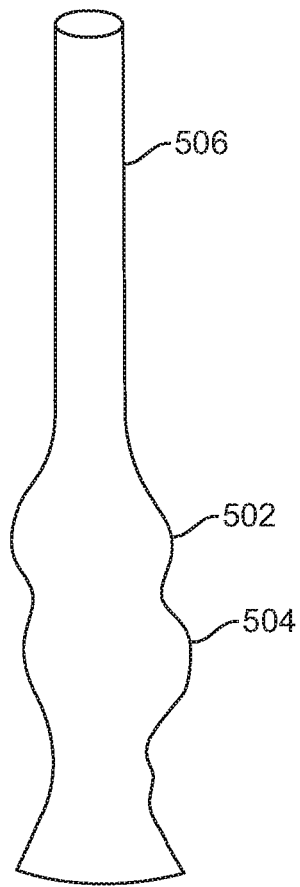
FIGS. 5A-5C illustrate another exemplary embodiment of a personalized prosthesis.
Figure 5B:
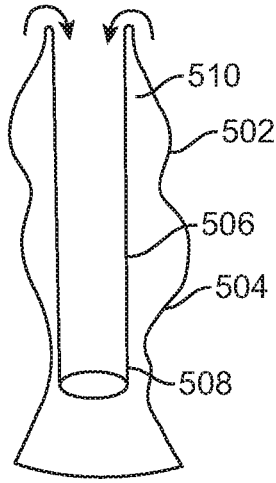
Figure 5C:
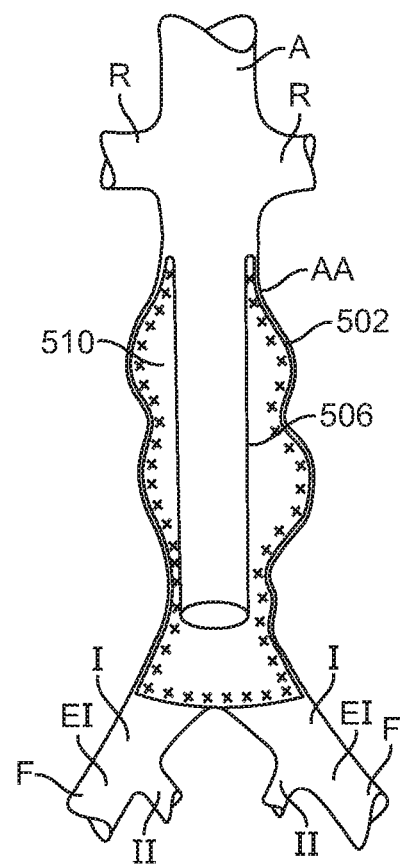

FIGS. 5A-5C illustrate an exemplary embodiment of a personalized prosthesis that forms a new lumen for blood flow. The aneurysm is imaged as described previously, and the corresponding mandrel is also manufactured to match the aneurysm similarly as described above. Once the mandrel is fabricated, the mesh and/or polymer may also be applied to the mandrel as discussed above. In this embodiment, the resulting prosthesis 502 includes a main body section 504 that matches the size and shape of the aneurysm, and also includes an elongated neck portion 506. In FIG. 5B, the elongated neck 506 may be invaginated as indicated by the arrows such that the elongated neck portion 506 becomes disposed inside the main body portion 504. The space 510, the neck portion 506, and the inside wall of the prosthesis 502 may be left as is, or it may be filled with a fluid, solid, or other material. The elongated neck portion 506 which preferably is a cylindrically shaped tube can now act as a lumen for blood flow therethrough. The free end 508 of the elongated neck 506 may be left as is, or it may be anchored to prevent flapping. Anchoring may be accomplished with a stent, sutures, staples, or it may be sized such that the blood pressure opens the free end up fully and lodges it against a downstream and inner portion of the prosthesis. The free end 508 may also be sealed with the prosthesis in case the space 510 is filled with a material. FIG. 5C illustrates the personalized prosthesis of FIG. 5B once it has been delivered into an infrarenal aortic aneurysm AA. This embodiment allows creation of a lumen which more accurately matches the natural blood flow path before the aneurysm enlarged the blood flow path. Delivery of the personalized prosthesis may be by any of the methods described herein.

In the embodiment of FIGS. 4A-4F a single prosthesis is delivered to the aneurysm. However, in other embodiments, more than one prosthesis may be delivered. Using multiple prostheses facilitates delivery of the prosthesis since a single, low profile device may be delivered. Multiple prostheses are then delivered on top of one another, or axially spaced apart from one another in order to provide the desired coverage and support. For example, FIGS. 6A-6B illustrate the use of two prostheses.

Figure 6A:
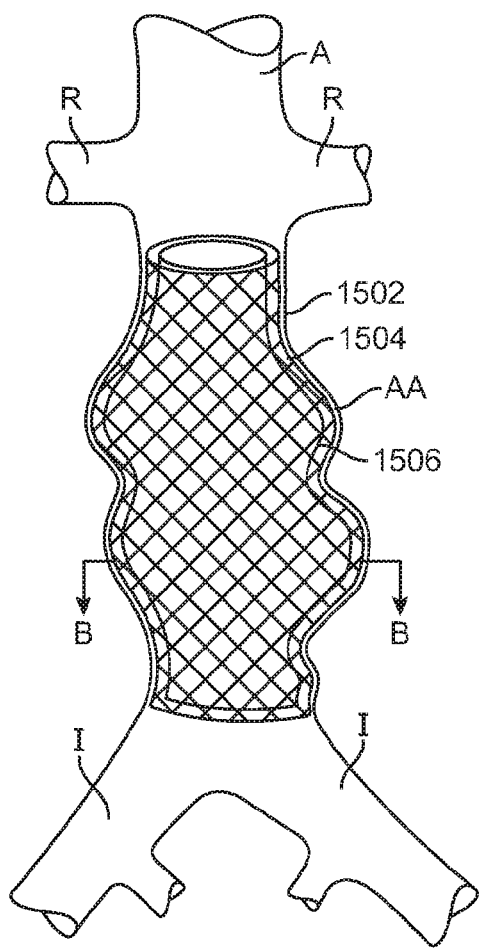
FIGS. 6A-6B illustrate an exemplary use of multiple prostheses.
Figure 6B:
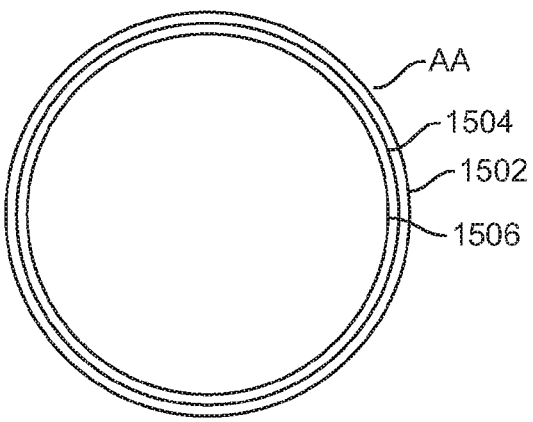

The prostheses in FIGS. 6A-6B may be delivered in substantially the same manner as previously described above, one after the other. A first personalized prosthesis 1504 is delivered to the aneurysm AA and allowed to expand into engagement with the wall 1502. A second personalized prosthesis 1506 is then serially delivered afterward so that it sits inside the first prosthesis 1504. FIG. 6B illustrates a cross-section taken along the line B-B in FIG. 6A and shows the two prostheses adjacent one another in the aneurysm. This provides greater support to the aneurysm and allows two lower profile prostheses to be delivered instead of a single higher profile device. Endothelialization of the prostheses will help anchor them into position. Endothelialization begins about two weeks after implantation and is generally complete after about two months. Multiple prostheses may be stacked inside one another, and/or they be placed end to end to cover a longer treatment region.

Figure 7:
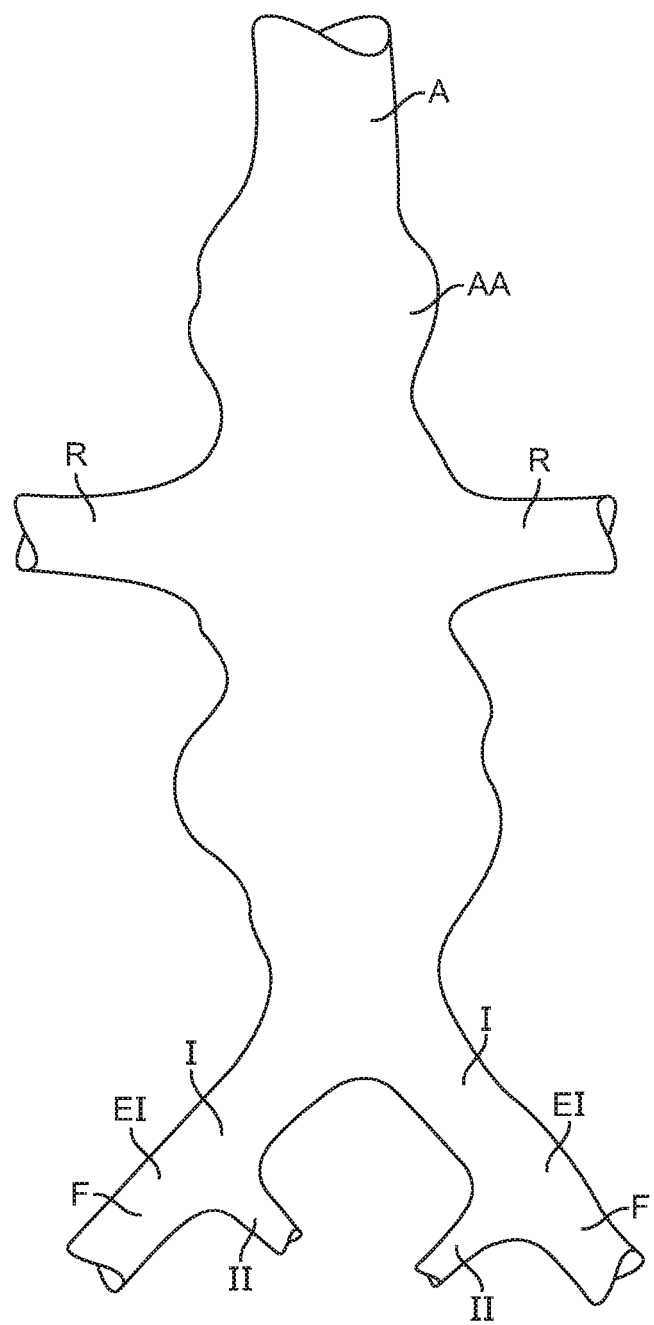
FIG. 7 illustrates a juxtarenal aneurysm.

Other aneurysms may involve side branch vessels. A personalized mesh prosthesis with a polymer or fabric coating may be used, but the prosthesis will obstruct blood flow into the side branch vessels. A mesh only personalized prosthesis may be used to solve this challenge, because a wire in the mesh may be disposed over the ostium of the side branch without substantially blocking blood flow to the side branch. Thus implanting a standard prosthesis to exclude the aneurysm could obstruct the side branch vessels preventing proper blood flow. For example, a juxtarenal aneurysm AA is seen in FIG. 7 and extends across part of the aorta A, and involves the renal arteries R. In this exemplary aneurysm, the iliac arteries I, external iliacs EI, internal iliacs II, and femoral arteries F remain unaffected by the aneurysm. Implanting a prosthesis and excluding the aneurysm would obstruct blood from flowing into the renal arteries resulting in damage to the kidneys. Thus, an improved and personalized prosthesis not only has a size and shape to match the anatomy of the treatment site, but also can accommodate for side branch vessels, or other side branch lumens and passageways.

Figure 8:
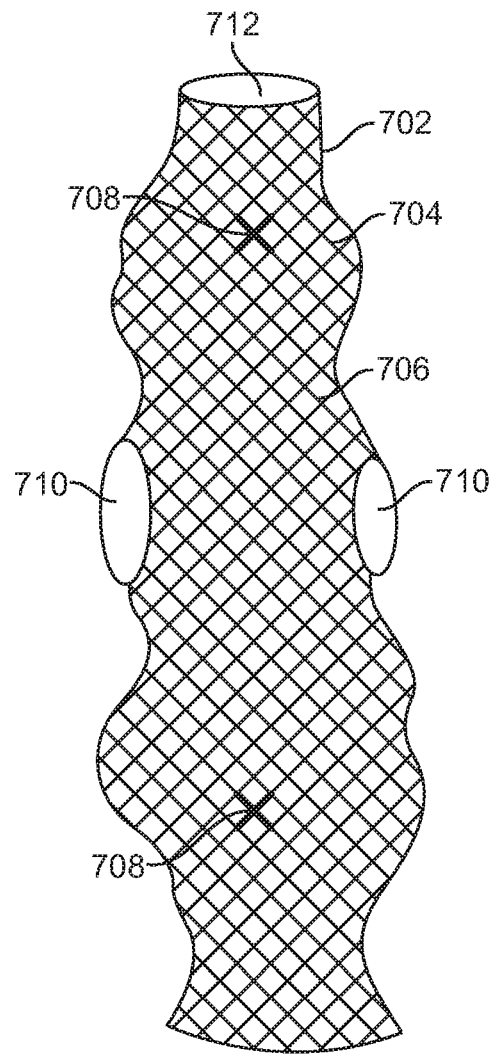
FIG. 8 illustrates a personalized prosthesis that accommodates side branch vessels.
Figure 9:
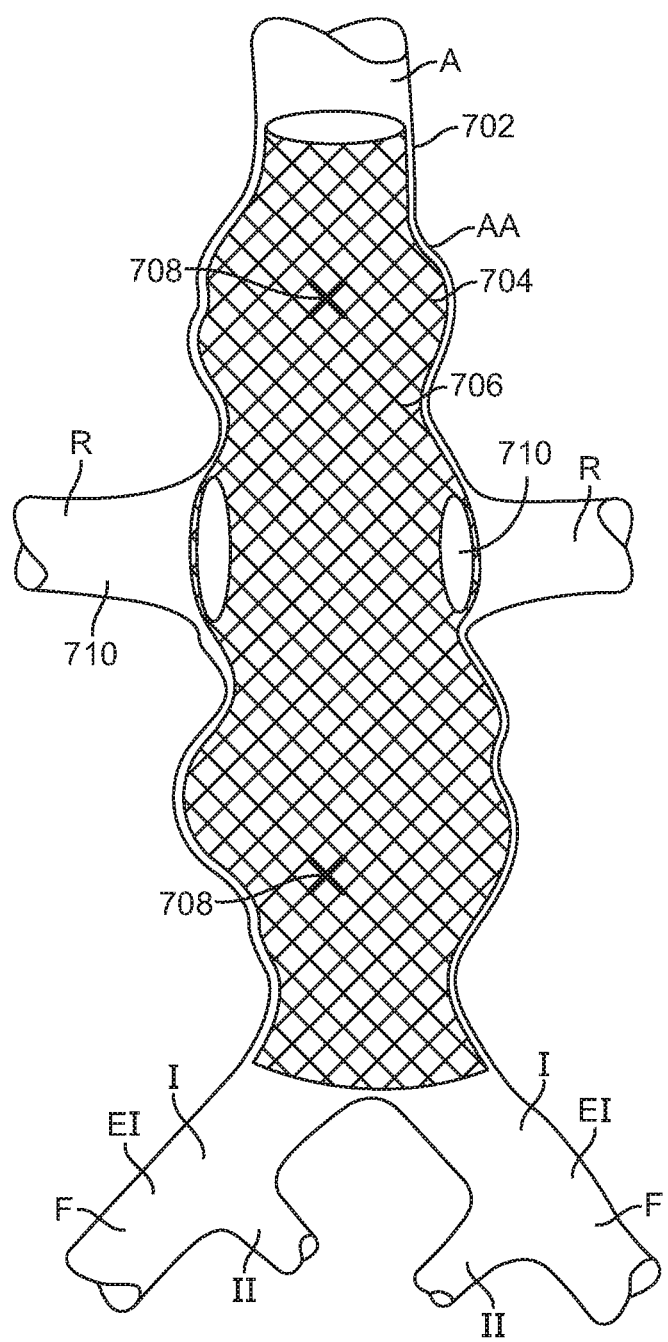
FIG. 9 illustrates implantation of the prosthesis in FIG. 7 in a juxtarenal aneurysm.

FIG. 8 illustrates an exemplary embodiment of a personalized prosthesis that can accommodate side branches such as the renal arteries. The personalized prosthesis 702 includes a wire mesh 704 and an optional polymer or fabric cover 706 similar to previous embodiments described herein. The prosthesis 702 may also optionally include radiopaque markers 708 to facilitate visualization and placement. The personalized prosthesis may be fabricated in a similar manner as described above, and also includes apertures 710 in a sidewall of the prosthesis that are in fluid communication with the central channel 712 of the prosthesis. The side apertures are positioned along the prosthesis so that they match the location of the side branch vessels or body passages. The location of the apertures is accurately determined based on the image obtained, such as a a CT scan and the like. During manufacturing of the prosthesis, additional mandrels that extend laterally away from the main forming mandrel may be coupled with the main forming mandrel. This maintains the apertures in the wire mesh, and also maintains the apertures once the mesh and mandrel are dip coated into a polymer, or when a polymer or fabric cover are otherwise applied to the mesh. The prosthesis 702 can then be loaded into a delivery catheter as previously described. The prosthesis is then deployed using the radiopaque markers so that the side apertures 710 align with the ostia of the side branch vessels. FIG. 9 shows the prosthesis 702 deployed in the juxtarenal aneurysm of FIG. 7, with the apertures 710 aligned with the ostia of the renal arteries R. Thus blood flow is not only maintained through the prosthesis across the aneurysm, but also to the renal arteries. The filaments in the prosthesis do not obstruct blood flow to the side branches. While the filaments may partially cover the ostia, this is not significant enough to affect blood flow.

Figures 10A, 10B:
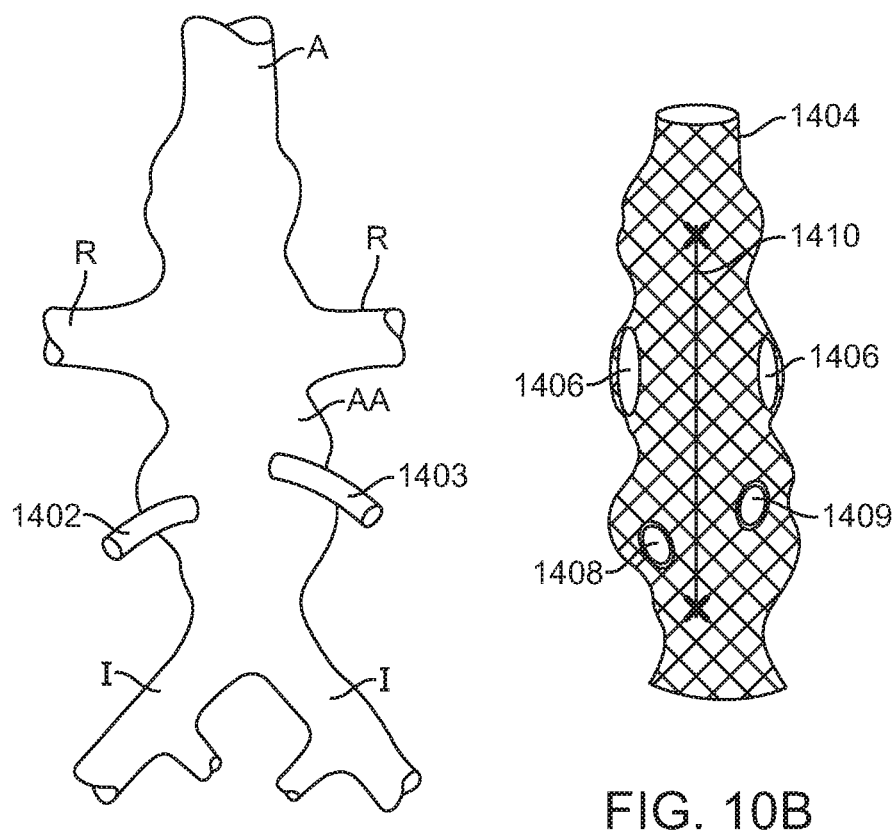
FIGS. 10A-10B illustrate an exemplary embodiment of a prosthesis accommodating side branches.

FIGS. 10A-10B illustrate another embodiment of a personalized prosthesis that accommodates for the renal arteries as well as other side branch vessels. In FIG. 10A the aneurysm AA is disposed in the aorta A and extends across the renal arteries R and also across other side branch vessels 1402 and 1403 that are between the iliac arteries I and the renal arteries R. The aneurysm is imaged as described before, and a central mandrel matching the aneurysm is then fabricated. Additional mandrels are laterally positioned where the renal arteries and the side branches are located. The mesh is then woven over the mandrel and around the side branch mandrels so that an aperture is maintained at their location. In alternative embodiments, the mesh is pre-woven and the loaded over the mandrel. The side branch mandrels are placed into the mandrel to push the filaments of the mesh away thereby creating and preserving openings for the renal or other side branches. After heat treating and other processing including putting an optional polymer or fabric coating over the mesh, a personalized prosthesis 1404 is produced as seen in FIG. 10B. Any of the mesh patterns disclosed herein may be used. The prosthesis then includes apertures 1406 that will match with the ostia to the renal arteries, and also apertures 1408 and 1409 will match with the other two side branches. The apertures 1406, 1408 and 1409 are in fluid communication with the central channel of the prosthesis so that blood flow will remain unobstructed to the renals or side branches. An optional radiopaque marker 1410 may also be included on the prosthesis in order to help align the prosthesis with the renal arteries and side branches during delivery. The radiopaque marker may include a long linear portion that indicates the longitudinal axis of the prosthesis. The radiopaque marker may be formed from a dense metal such as gold or platinum, or rhodium alloy that is coupled to the mesh. The renal arteries or other side branches themselves may be used during alignment by injecting contrast media through the vessels while visualizing the prosthesis and surrounding vessels under fluoroscopy or using other visualization techniques known in the art.

The personalized prostheses described above preferably include a wire mesh that self-expands to the personalized shape. Various wire patterns may be used to create the mesh.

Figure 11:
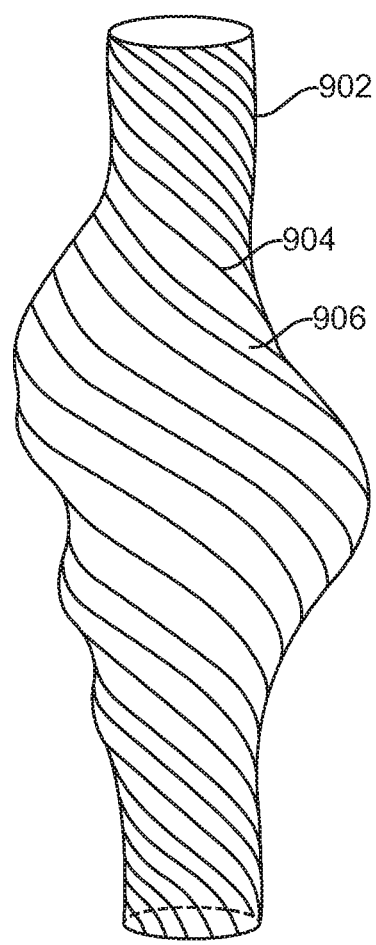
FIG. 11 illustrates an exemplary mesh.
Figure 12B:
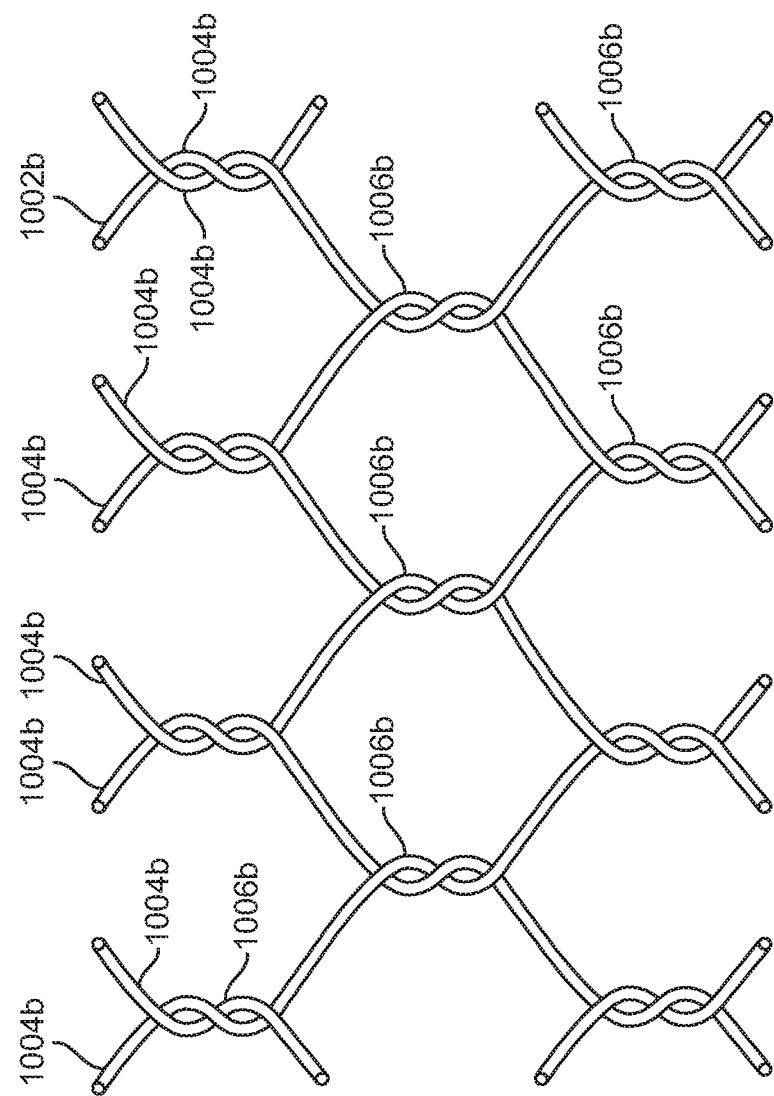

For example, FIG. 11 illustrates a mesh 902 having one or more filaments 904 which are spirally wound and an optional polymer or fabric cover 906 is applied to the mesh. This pattern of forming the mesh is advantageous because there is no overlap of the filaments, and the spiral pattern helps the mesh to be collapsed into a low profile for delivery. FIGS. 12A-12F illustrate other exemplary mesh patterns. FIG. 12A illustrates a mesh 1002a having one or more filaments 1004a that interweave with one another similar to traditional fencing wire or chicken wire, to form a single overlapping or twisted region 1006a. The overlap region is preferably in every row and every column of the mesh where the filaments meet. The overlapping region forms a protuberance which may be advantageous since the protuberance may help embed the prosthesis into the tissue at the treatment site thereby helping to anchor the prosthesis. Having a single overlap of the filaments helps the filaments move relative to one another thereby allowing the prosthesis to be easily collapsed which is desirable during loading onto a delivery system and also helps to keep the profile of the prosthesis minimal. This is also advantageous since it allows the prostheses to expand and collapse in concert with the pulsatile nature of the blood as it flows through the aorta or other vessel. However, in some circumstances, the single overlapping or twisted region may not be secure enough to keep the mesh in its formed pattern or to provide adequate support to the aneurysm, especially when the prosthesis is under tension or compression because the wires in the mesh may slip or slide relative to one another. The prosthesis undergoes tension and compression during loading on a delivery system, during deployment, and after implantation due to the pulsatile nature of blood flow.

FIG. 12B illustrates an alternative embodiment of a mesh pattern that is more secure than the embodiment of FIG. 12A. Mesh 1002b has one or more filaments 1004b that interweave with one another to form a double overlapping or twisted region 1006b. The overlap region is preferably in every row and every column of the mesh where the filaments meet. The overlap region forms a protuberance similar to that in FIG. 12A and thus may also be useful in anchoring the prosthesis. Having the double overlapped or twisted region secures the filaments together more tightly and thus helps prevents the filaments from slipping or sliding relative to one another when the prosthesis is under tension or compression. Thus the prosthesis retains its shape and provides more support than the embodiment in FIG. 12A. However, in some circumstances, the wires may still slip or slide relative to one another, thus further securing of the filaments may be needed.

Figure 12C:
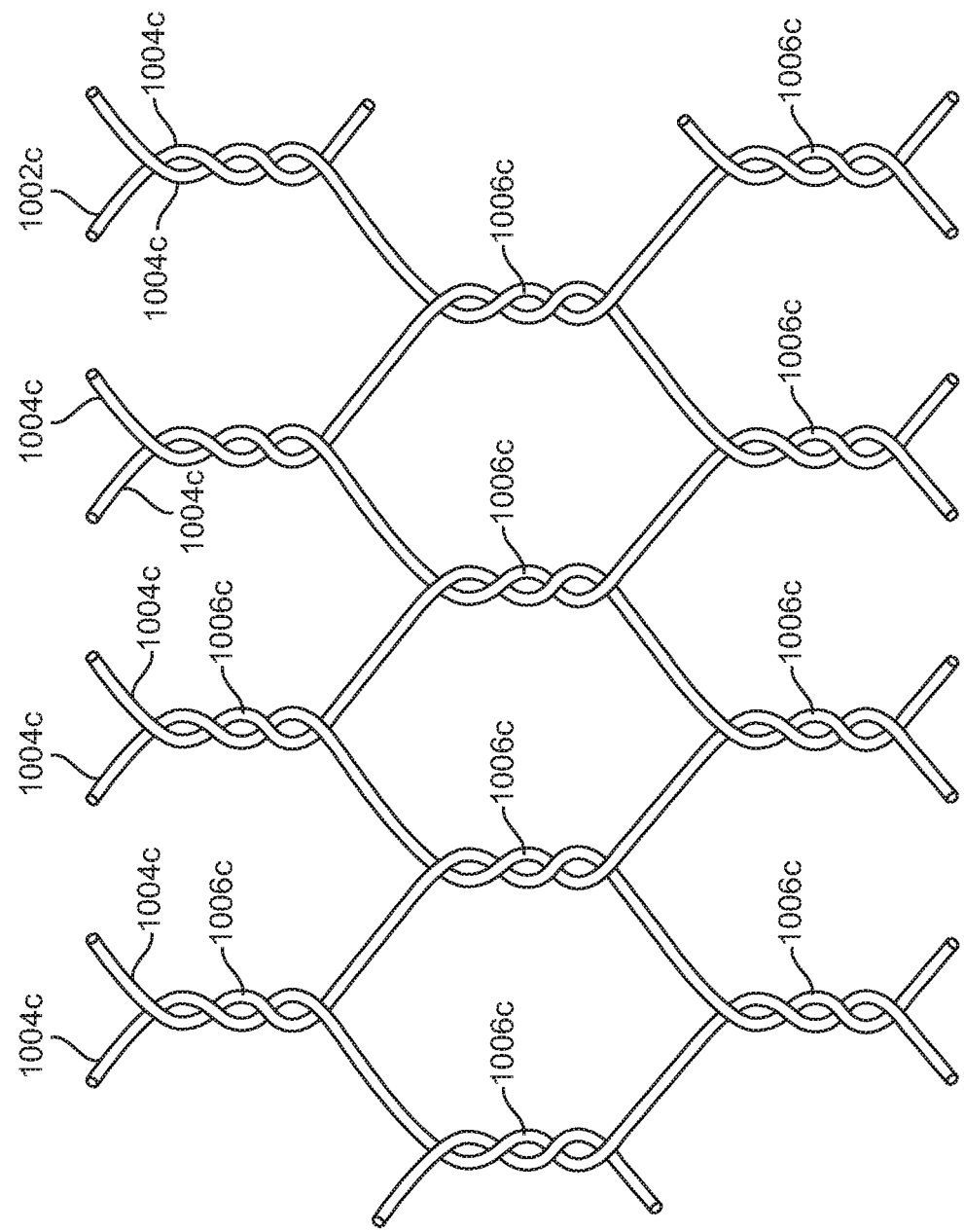

FIG. 12C illustrates still another embodiment of a mesh pattern which helps provide a stable mesh. The mesh 1002c has one or more filaments 1004c that interweave with one another to form a triple overlapping or twisted region 1006c. The overlap region is preferably in every row and every column of the mesh where the filaments meet. The overlap forms a protuberance similar to those previously discussed and therefore may aid in anchoring of the prosthesis. Having the triple overlap or twisted region secures the filaments together even more tightly than in the previous embodiments and thus the filaments are further constrained from slipping or sliding relative to one another when the prosthesis is under tension or compression. In some circumstances, having the triple overlap region secures the filaments together tightly enough that they cannot move at all relative to one another when the prosthesis is under tension or compression. If the filaments cannot move at all relative to one another, this prevents the prosthesis from axially or radially expanding or contracting which interferes with its ability to be loaded in a collapsed configuration onto a delivery system, from expanding radially outward upon deployment, or from expanding an contracting in concert with the vessel wall due to pulsatile blood flow.

Figure 12D:
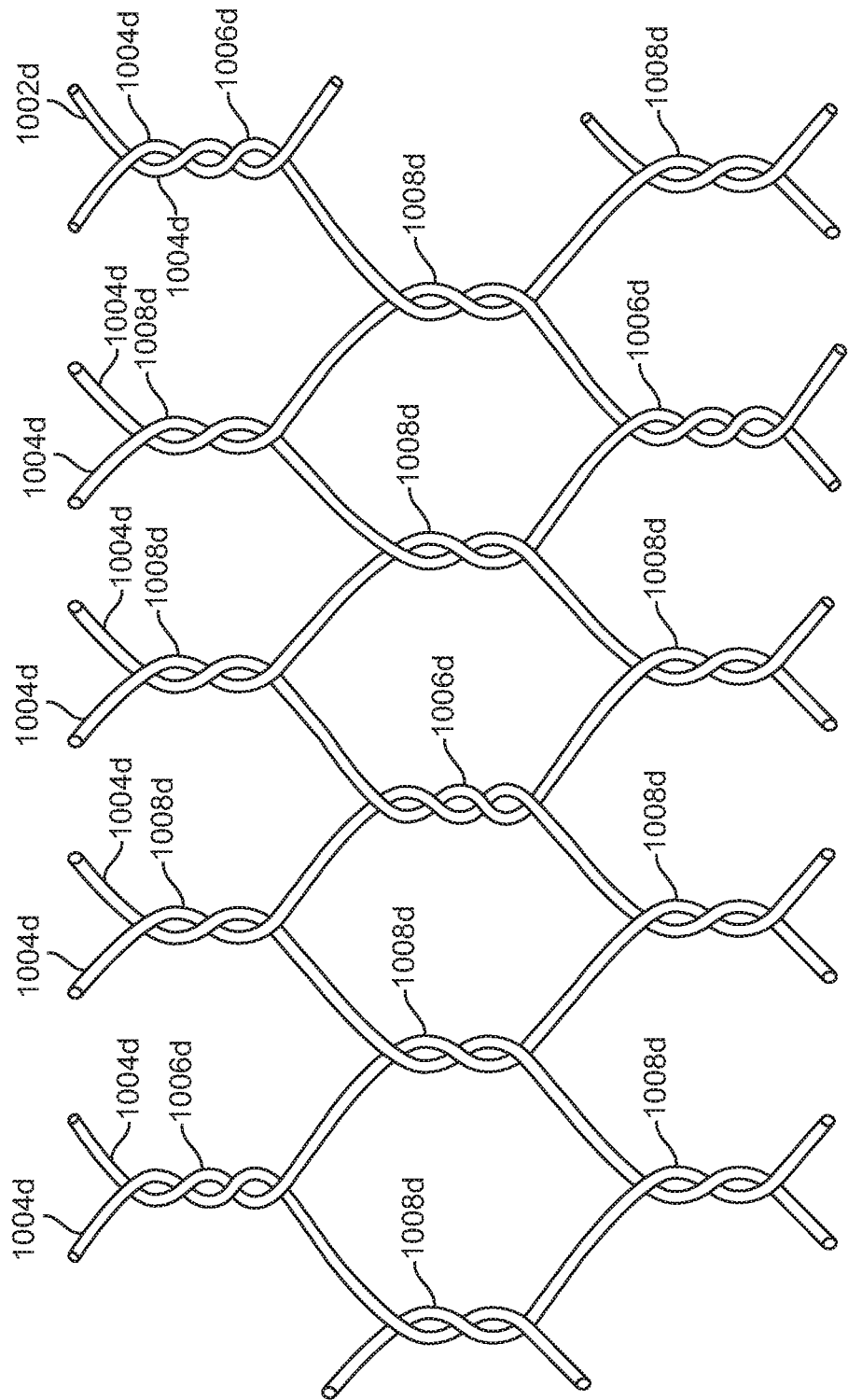

FIG. 12D illustrates a preferred embodiment of a hybrid mesh pattern that secures the filaments together securely so that the prosthesis holds its shape and provides good support during tension and compression, and yet at the same time still allows some movement between the filaments so that the prosthesis can expand and contract. Mesh 1002d has one or more filaments 1004d that interweave with one another to form an alternating pattern of a triple overlap or twisted region 1006d followed by three double overlapped or twisted regions 1008d. The pattern then repeats itself horizontally, and the next row shifts by one twist to the right. Thus the triple twist in one row is offset from the triple twist in the next row. followed by another double or twisted overlap region 1008d, and then the pattern repeats. The pattern repeats so that everywhere the filaments overlap with one another, there is either a double or triple overlap or twisted region. The overlap region forms a similar protuberance as previously described which may be useful for anchoring the prosthesis. This hybrid weave has the advantages of both the double and triple overlap weaves previously described. Thus, the triple overlap regions secure the filaments together to minimize their movement relative to one another during compression or tension and thus the prosthesis holds its shape and provides good support, while at the same time the double overlap regions allow some movement of the filaments relative to one another thereby allowing the prosthesis to axially and radially expand and contract during delivery, deployment, and after implantation. The weave preferably minimizes or substantially eliminates axial expansion and contraction while allowing radial expansion and contraction.

Figure 12E:
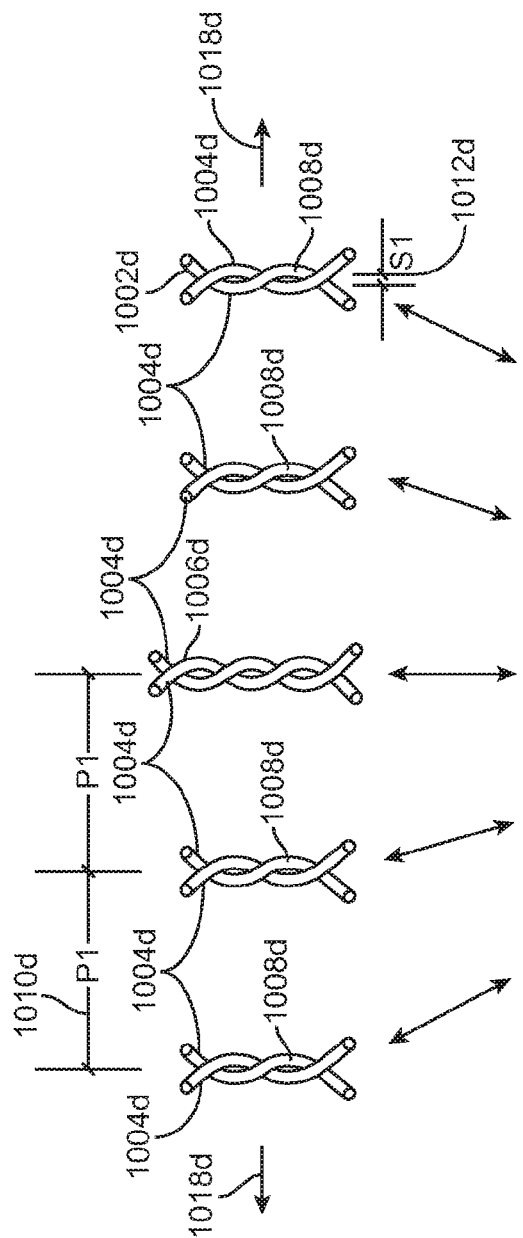
Figure 12F:
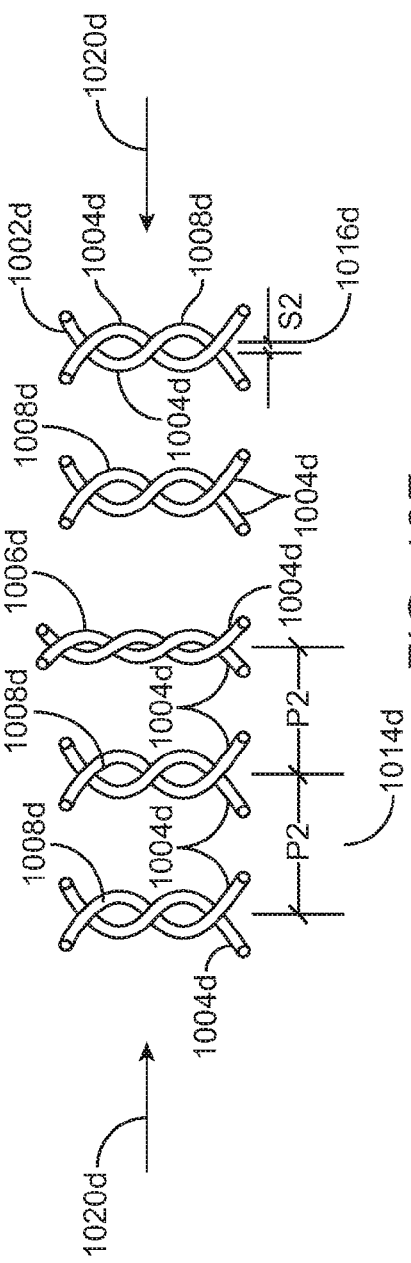

FIGS. 12E-12F illustrates expansion and contraction of a personalized prosthesis such as those described above using the weave of FIG. 12D. Without being bound by any particular theory, it is believed that the filaments will remain tightly engaged with one another when the prosthesis 1002d is under tension such as while the heart is in systole as seen in FIG. 12E and represented by arrows 1018d. Here, the filaments 1004d remain tightly wound together in both the double overlap region 1008d as well as the triple overlap region 1006d. The gap 1012d between adjacent filaments wound together in a region 1008d may be represented by distance S1 and the pitch 1010d or spacing between adjacent columns of wound filaments may be represented by distance P1 during systole. When the prosthesis is compressed such as when the heart is in diastole, as indicated by arrows 1020d in FIG. 12F, the pitch or spacing 1014d between adjacent columns of wound filaments generally decreases relative to the expanded configuration. Moreover, the gap 1016d between adjacent filaments wound together in a double overlap region 1008d increases relative to the when the prosthesis is in the expanded configuration thereby allowing the filaments to slide relative to one another. The gap between adjacent filaments wound together in a triple overlap region remain twisted together and there is substantially no relaxation. Thus, when viewing the prosthesis laying on its side with its longitudinal axis horizontal, the triple-double-double-double horizontal weave pattern accommodates the motion of the aorta vessel wall caused by the pulsatile motion of the blood flowing through it. Of course, one of skill in the art will appreciate that this particular pattern is not intended to be limiting. Other patterns may be used including any combination or permutation of the single, double, triple, or more than three overlapping regions.

Figure 13:
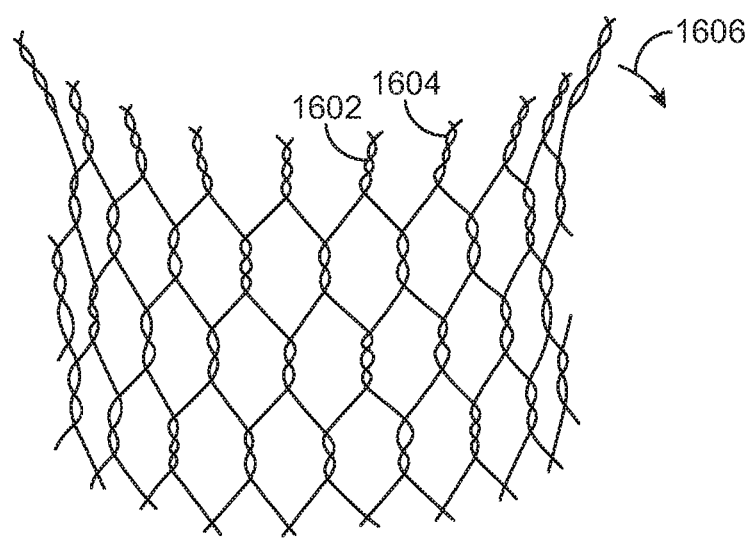
FIG. 13 illustrates an exemplary embodiment of an end of a prosthesis.

The filaments on the proximal and distal ends of the prosthesis may be terminated in any number of ways. FIG. 13 illustrates one exemplary embodiment. The prosthesis 1602 has the triple-double-double-double weave pattern of FIGS. 12A-12F described above. The filaments may terminate in an end region 1604 by twisting the filaments such that they overlap one another four times. One of skill in the art will appreciate that this is not intended to be limiting and the number of overlapping regions may be one, two, three, four, five, six, or more. Additionally, the ends may remain extending axially outward to help anchor the prosthesis in tissue by partially piercing the tissue, or the ends may be formed into curves, loops, or other shapes to prevent sharp ends from protruding and causing tissue trauma. This prevents the filaments from moving relative to one another. Additionally, the end region 1604 may then be bent slightly radially outward 1606 to form a skirt or flanged region which flares outward and thus can embed into the vessel wall to help anchor the prosthesis.

Figure 14:
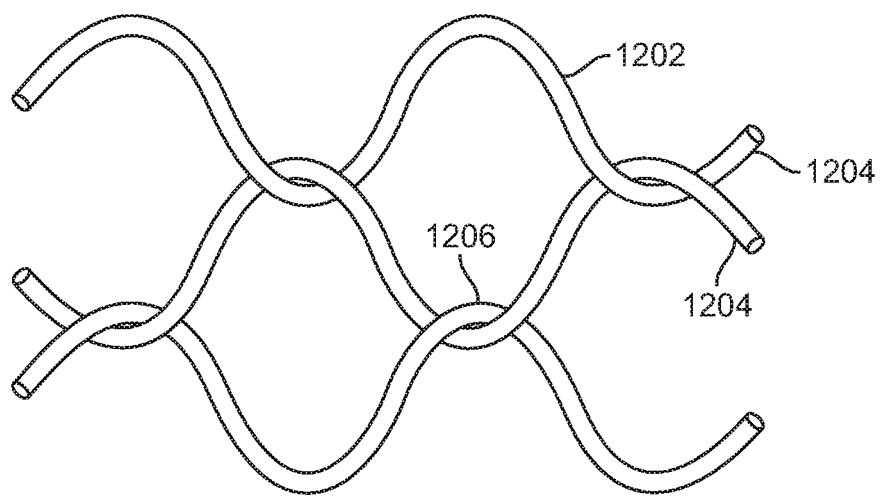
FIG. 14 illustrates an exemplary mesh.

In the embodiments of FIGS. 12A-12F, the weave pattern has been described when the prosthesis is sitting on its side such that the longitudinal axis of the prosthesis is generally horizontal. Thus, the weave pattern is generally parallel to the longitudinal axis, and the filaments are weaved together in a horizontal pattern across the prosthesis and with a vertical orientation. In still other embodiments, the weave pattern of FIGS. 12A-12F may be rotated ninety degrees so that the filaments are weaved an orthogonal direction. FIG. 14 illustrates an exemplary embodiment of the weave pattern in FIG. 12A rotated ninety degrees. The weave is illustrated with the prosthesis laying flat on its side with its longitudinal axis generally horizontal. Thus, mesh 1202 includes a plurality of filaments 1204 that are weaved together to form a single overlap or twisted region 1206. Other aspects of this embodiment generally take the same form as in FIG. 12A. The other embodiments described previously may also be weaved in a pattern that has been rotated ninety degrees. Any of the mesh patterns described herein may be formed into a round tubular member or the mesh may be woven into a flat sheet and the ends may be joined together to form a round tubular member. Additionally wires or filaments of different diameters may be combined with one other, or a single diameter may be used throughout a single mesh prosthesis in order to obtain desired mechanical properties.

Figure 15:
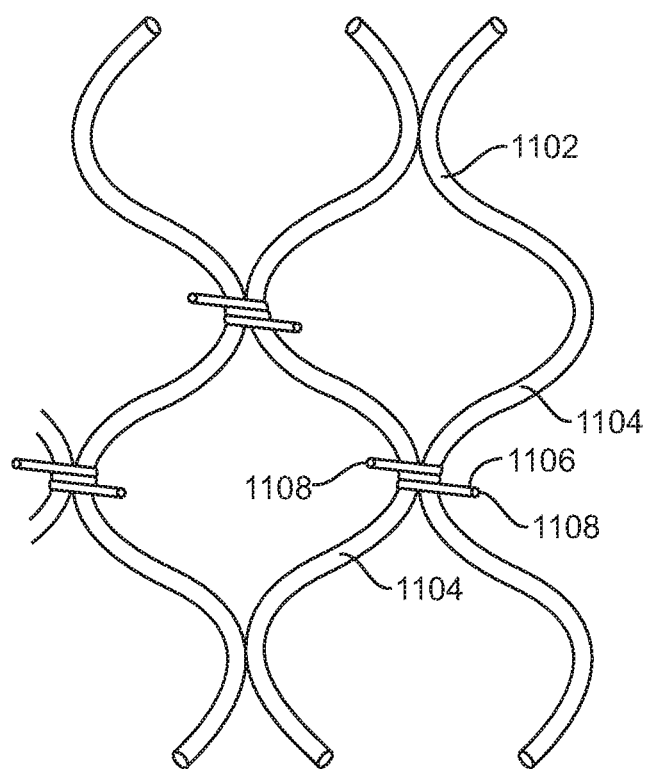
FIG. 15 illustrates another exemplary embodiment of a mesh pattern.

FIG. 15 illustrates still another pattern for the mesh 1102. This pattern has one or more filaments 1104 woven into an undulating pattern. Adjacent rows of the undulating filaments are tied together with a wire, suture, or other tie 1106. Optionally, one or both ends of the tie 1106 may be left uncut to form a barb 1108 that can also be used to help anchor the prosthesis to tissue at the treatment site. Any of these wire mesh patterns with anchoring or without anchoring may be used in any of the embodiments described herein.

Figure 16:
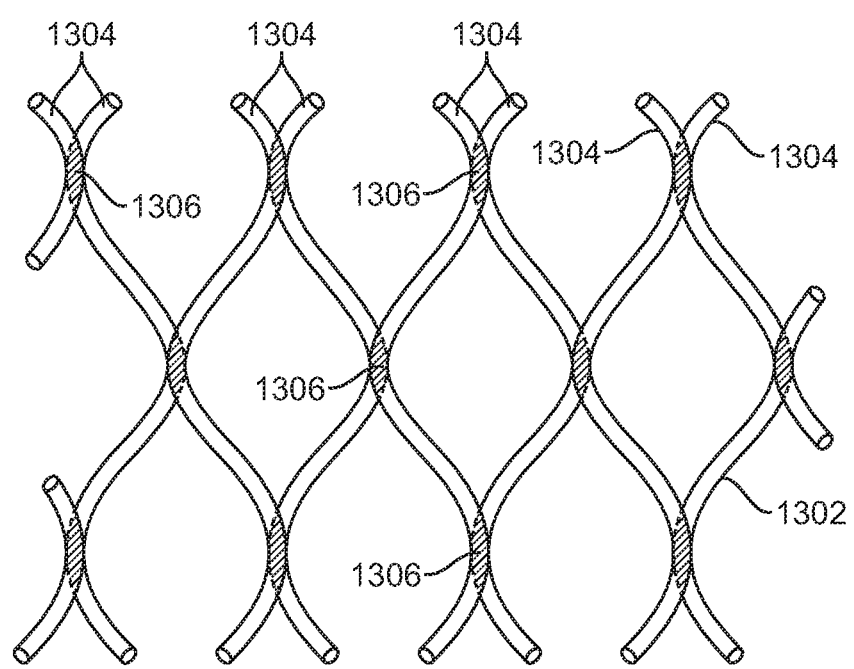
FIG. 16 illustrates yet another exemplary embodiment of a mesh.

FIG. 16 illustrates yet another exemplary embodiment of a mesh. The mesh 1302 includes one or more filaments 1304 which are formed into an undulating pattern having peaks and valleys. The peaks and valleys in one row of the mesh may overlap with the valleys and peaks of an adjacent row of the mesh. The overlapping portions may then be welded 1306 together to keep the filaments coupled together. In alternative embodiments, welds may be any combination of the previous mesh embodiments.

In any of the embodiments described herein, the filament may be any combination of wires having any cross-section such as round, square, rectangular, etc. and the size of the wire may be adjusted in order to various properties of the prosthesis such as its profile in the collapsed configuration, its stiffness and strength, and other properties. In preferred embodiments, a round nitinol wire is used having a diameter of 0.005 inches to 0.006 inches. Exemplary wire diameters of 0.005 inches, 0.0055 inches, and 0.006 inches may be used.

Additionally, any of the prostheses may carry a therapeutic agent such as an antithrombotic agent, antibiotic, etc. for localized and controlled elution at the treatment site. One of skill in the art will also appreciate that the prosthesis described herein preferably has a mesh with a polymer or fabric cover disposed thereover, but the prosthesis could be a mesh only to support the damaged or diseased tissue, or the prosthesis could be the polymer or fabric cover only. Thus, the fabrication methods and delivery methods described herein apply to either embodiment of prosthesis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating tissue at a treatment site having a shape and a volume, said method comprising:
   providing a prosthesis having an expanded configuration and a collapsed configuration, wherein the prosthesis is personalized to match the shape and the volume of the treatment site, and wherein the prosthesis is formed from a mesh comprising a plurality of filaments twisted together to form a repeating circumferential pattern of three twists followed by two twists followed by two twists;
   advancing the prosthesis in the collapsed configuration to the treatment site;
   self-expanding the prosthesis into the expanded configuration thereby engaging the tissue at the treatment site and conforming to the shape and the volume of the of the treatment site; and
   reinforcing the tissue with the prosthesis.

2. The method of claim 1, wherein the prosthesis comprises a self-expanding wire mesh surrounded by a polymer cover.

3. The method of claim 1, wherein the prosthesis comprises a self-expanding wire mesh.

4. The method of claim 1, wherein the prosthesis comprises a resilient polymer.

5. The method of claim 1, wherein the prosthesis further comprises a lumen extending therethrough and having a shape, wherein the lumen shape substantially matches the shape of the treatment site.

6. The method of claim 5, wherein the lumen does not substantially alter a blood flow path across the treatment site.

7. The method of claim 1, wherein the prosthesis further comprises a cylindrical lumen extending therethrough.

8. The method of claim 7, wherein the lumen is formed from an invaginated portion of the prosthesis.

9. The method of claim 1, wherein advancing the prosthesis comprises advancing the prosthesis through a blood vessel.

10. The method of claim 1, wherein radially expanding the prosthesis comprises retracting a sheath away from the prosthesis, thereby allowing the prosthesis to self-expand into the expanded configuration.

11. The method of claim 1, wherein reinforcing the tissue comprises anchoring the prosthesis to the tissue.

12. The method of claim 1, wherein the treatment site comprises an aneurysm, and reinforcing the tissue comprises preventing the aneurysm from enlarging.

13. The method of claim 1, wherein the treatment site comprises an aneurysm and reinforcing the tissue comprises excluding the aneurysm.

14. The method of claim 1, wherein anchoring the implantable prosthesis comprises engaging barbs on the prosthesis with the tissue.

15. The method of claim 1, wherein reinforcing comprises constraining the tissue from moving radially outward or radially inward.

16. The method of claim 1, wherein the prosthesis comprises one or more radiopaque markers, the method further comprising aligning the one or more radiopaque markers with one or more anatomical features at the treatment site.

17. The method of claim 1, wherein the prosthesis comprises one or more apertures in a sidewall thereof, the method further comprising aligning the one or more apertures with one or more ostia of sidebranch vessels or body passages at the treatment site, thereby preventing obstruction of the one or more sidebranch vessels or the body passages.

18. The method of claim 1, further comprising sealing the prosthesis against the tissue at the treatment site to prevent blood flow therepast.

19. The method of claim 1, wherein the repeating pattern further comprises two twists after the three twists followed by the two twist followed by the two twists.

* * * * *